(12) United States Patent
Imamura

(10) Patent No.: US 9,517,004 B2
(45) Date of Patent: Dec. 13, 2016

(54) INFORMATION PROCESSING APPARATUS, INFORMATION PROCESSING METHOD AND COMPUTER READABLE STORAGE MEDIUM

(71) Applicant: CANON KABUSHIKI KAISHA, Tokyo (JP)

(72) Inventor: Hiroshi Imamura, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 219 days.

(21) Appl. No.: 14/279,685

(22) Filed: May 16, 2014

(65) Prior Publication Data

US 2014/0347627 A1    Nov. 27, 2014

(30) Foreign Application Priority Data

May 27, 2013   (JP) .................................. 2013-111332

(51) Int. Cl.
*G06K 9/00* (2006.01)
*A61B 3/10* (2006.01)
(Continued)

(52) U.S. Cl.
CPC .......... *A61B 3/0016* (2013.01); *A61B 3/0033* (2013.01); *A61B 3/0058* (2013.01); *A61B 3/102* (2013.01); *A61B 3/1025* (2013.01); *A61B 3/14* (2013.01)

(58) Field of Classification Search
CPC ................ G06K 9/00; A61B 3/00; A61B 5/00
(Continued)

(56) References Cited

U.S. PATENT DOCUMENTS 6,078,681 A * 6/2000 Silver ................ G01N 21/6428
                                                           250/461.2
7,857,449 B2   12/2010 Imamura et al.
(Continued)

FOREIGN PATENT DOCUMENTS

CN    102438502 A    5/2012
EP    2 138 826 A1   12/2009
(Continued)

OTHER PUBLICATIONS

Communication, including Extended European Search Report, dated Oct. 24, 2014, cited in counterpart European Patent Application No. 14170109.4-1660.
(Continued)

*Primary Examiner* — Abolfazl Tabatabai
(74) *Attorney, Agent, or Firm* — Fitzpatrick, Cella, Harper & Scinto

(57) ABSTRACT

An information processing apparatus for controls, in one image capture region, image capture of a plurality of high-magnification images having a viewing angle smaller than the viewing angle of the image capture region. A presentation unit presents for selection a plurality of basic patterns each representing a distribution of positions at which to respectively capture high-magnification images. An adjustment unit adjusts, in accordance with an instruction of the operator, an image capture condition of the plurality of high-magnification images associated with the basic pattern selected from the plurality of basic patterns. A control unit causes an image capture apparatus to capture the plurality of high-magnification images in the image capture region in accordance with the adjusted image capture condition. An obtaining unit analyzes an image representing the entire image capture region of a magnification lower than that of
(Continued)

the high-magnification images and obtains information representing a feature of the image.

19 Claims, 16 Drawing Sheets

(51) Int. Cl.
*A61B 3/14* (2006.01)
*A61B 3/00* (2006.01)

(58) Field of Classification Search
USPC ........ 382/100, 117; 351/205, 206, 208, 209, 351/210, 246
See application file for complete search history.

(56) References Cited

U.S. PATENT DOCUMENTS

| | | | | |
|---|---|---|---|---|
| 8,132,914 | B2* | 3/2012 | Sakagawa | A61B 3/12 351/206 |
| 8,864,308 | B2* | 10/2014 | Sato | A61B 3/102 351/205 |
| 2010/0195050 | A1 | 8/2010 | Sakagawa | |
| 2010/0208204 | A1 | 8/2010 | Imamura et al. | |
| 2012/0044457 | A1 | 2/2012 | Sato et al. | |
| 2012/0249957 | A1* | 10/2012 | Shibata | A61B 3/0025 351/206 |
| 2013/0010262 | A1 | 1/2013 | Sato et al. | |
| 2013/0088686 | A1 | 4/2013 | Graziano et al. | |

FOREIGN PATENT DOCUMENTS

| | | |
|---|---|---|
| EP | 2 147 634 A1 | 1/2010 |
| EP | 2 692 274 A1 | 2/2014 |
| JP | 2012-213513 A | 11/2012 |
| WO | 2011/156797 A2 | 12/2011 |
| WO | 2013/125546 A1 | 8/2013 |

OTHER PUBLICATIONS

Chinese Official Action dated Sep. 2, 2015, issued in corresponding Chinese Patent Application No. 201410229107.3, with an English translation.

* cited by examiner

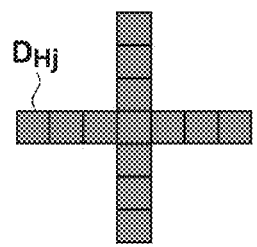
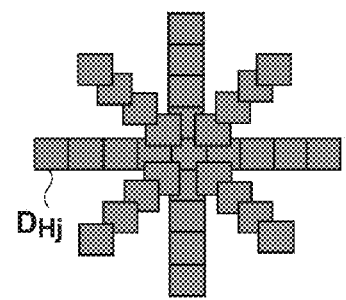
FIG. 6A          FIG. 6B          FIG. 6C
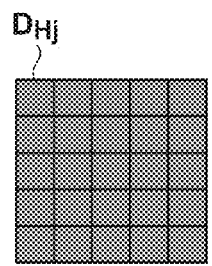
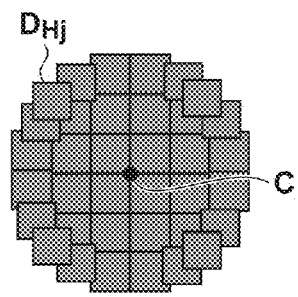
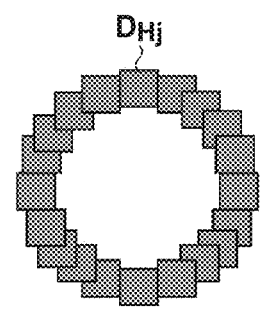
FIG. 6D          FIG. 6E          FIG. 6F

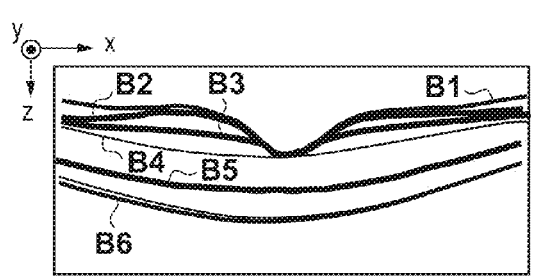
F I G. 7A
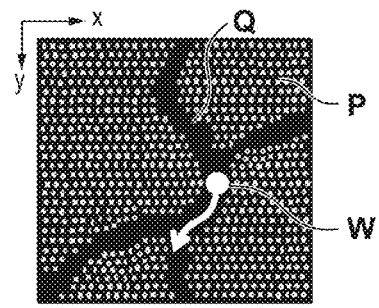
F I G. 7B
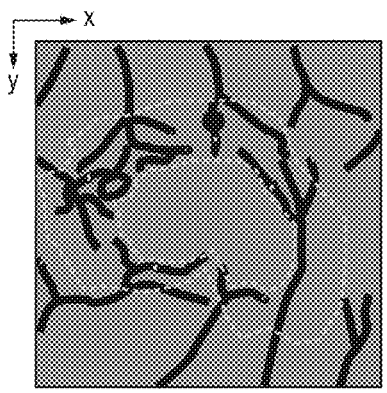
F I G. 7C
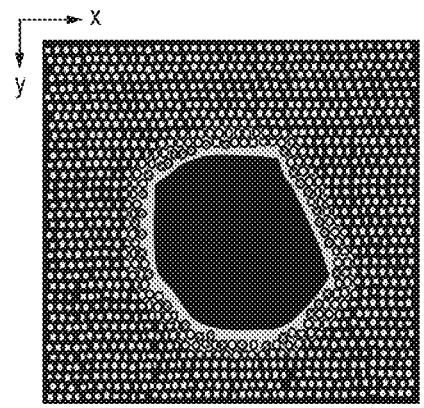
F I G. 7D
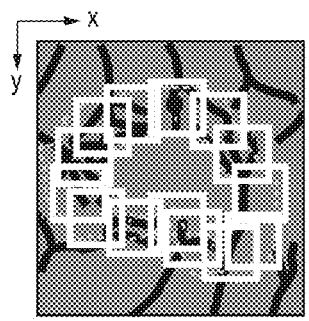
F I G. 7E
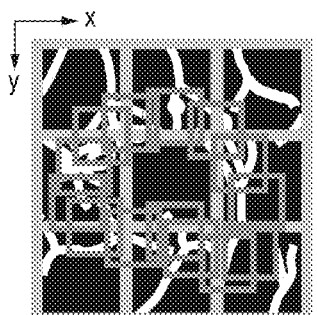
F I G. 7F
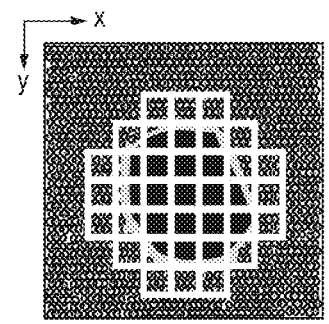
F I G. 7G

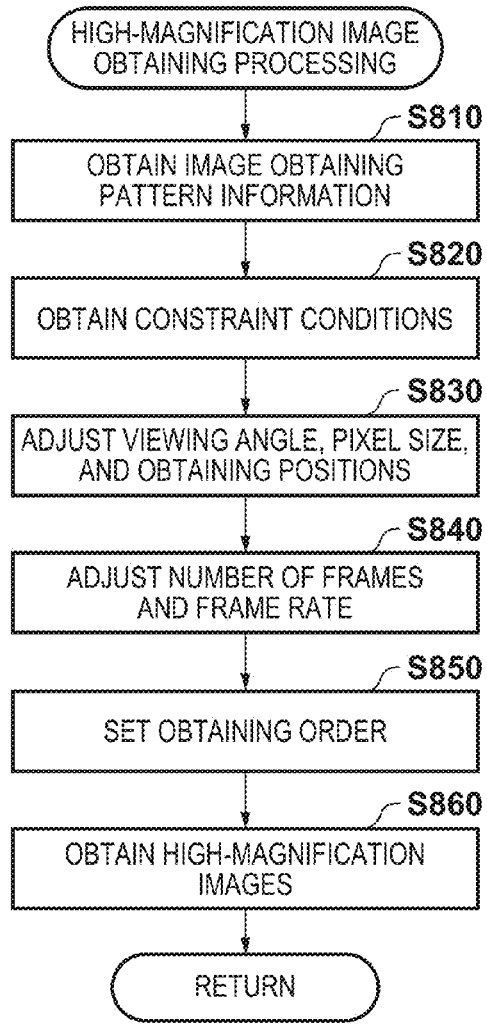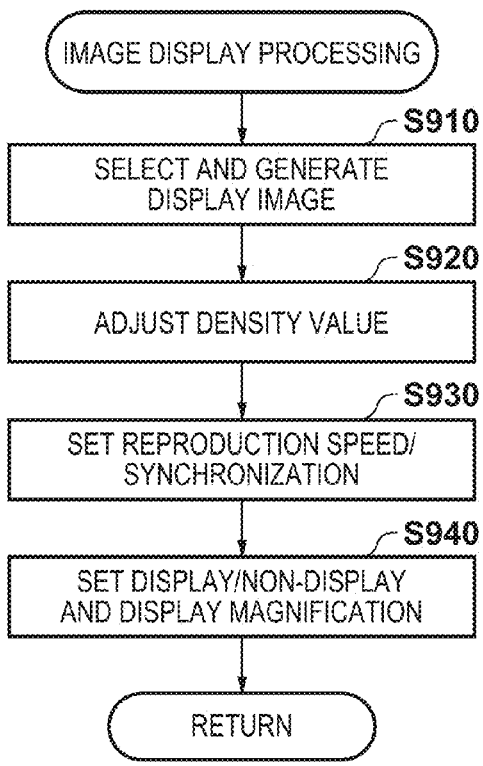
FIG. 8
FIG. 9

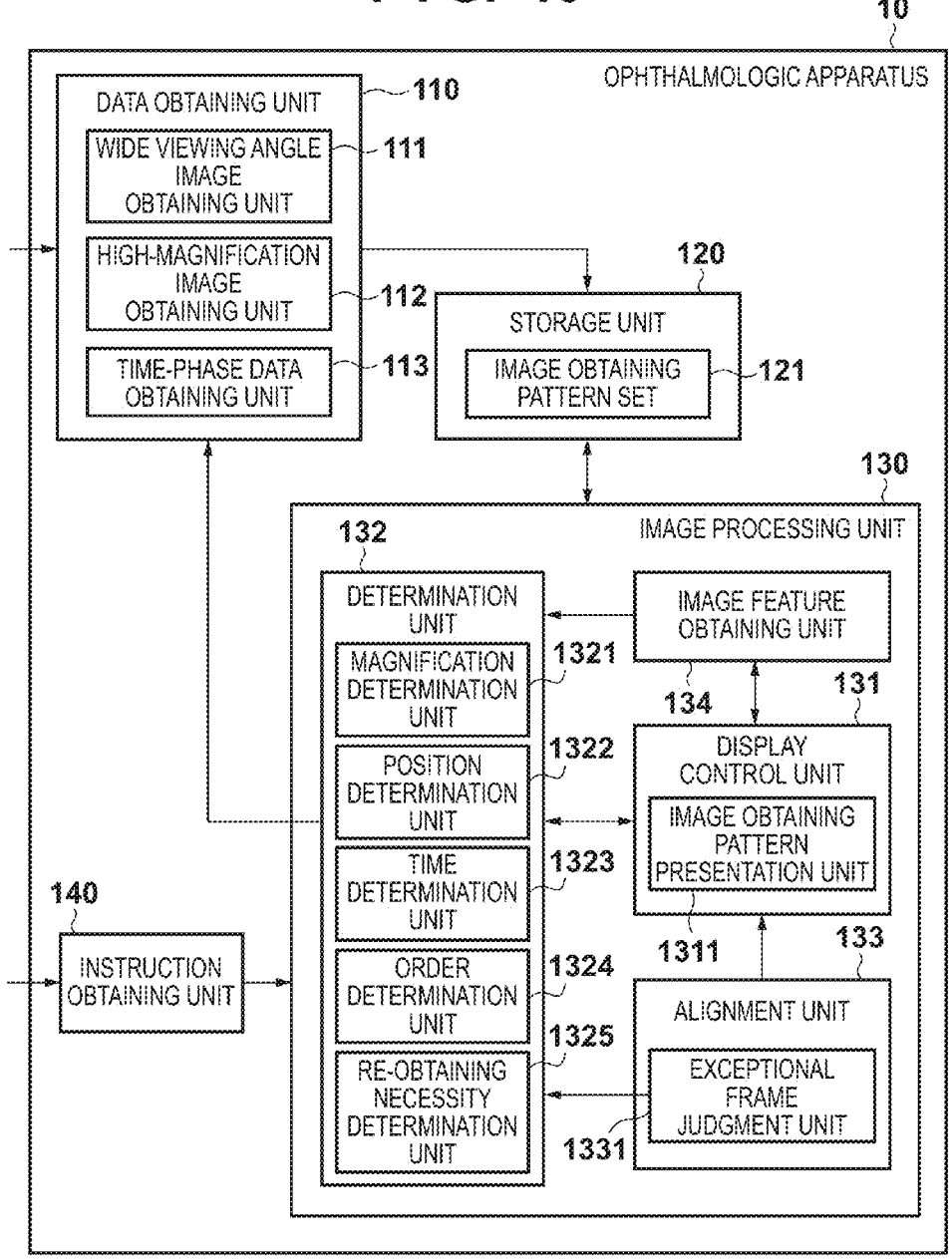

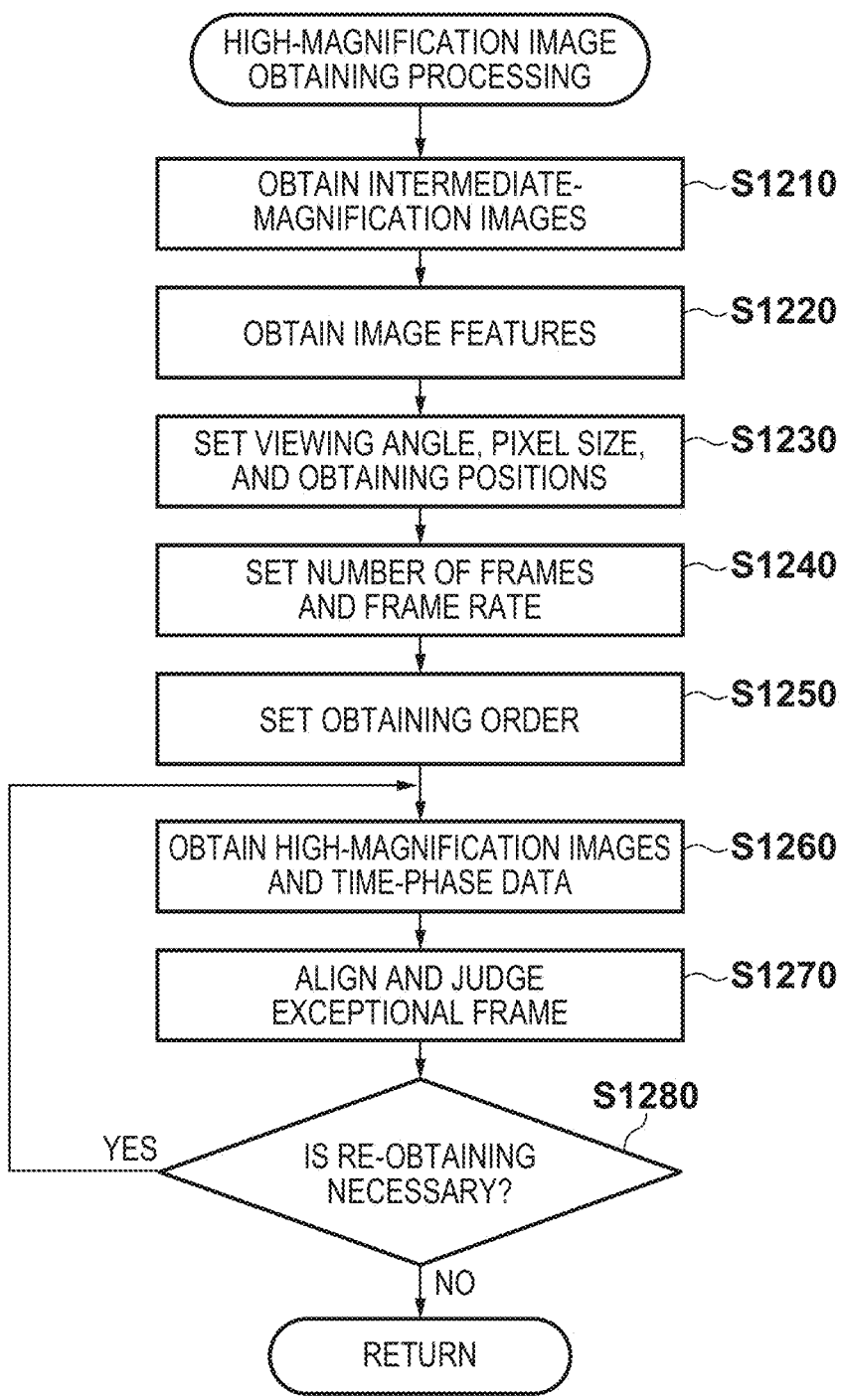

F I G. 13
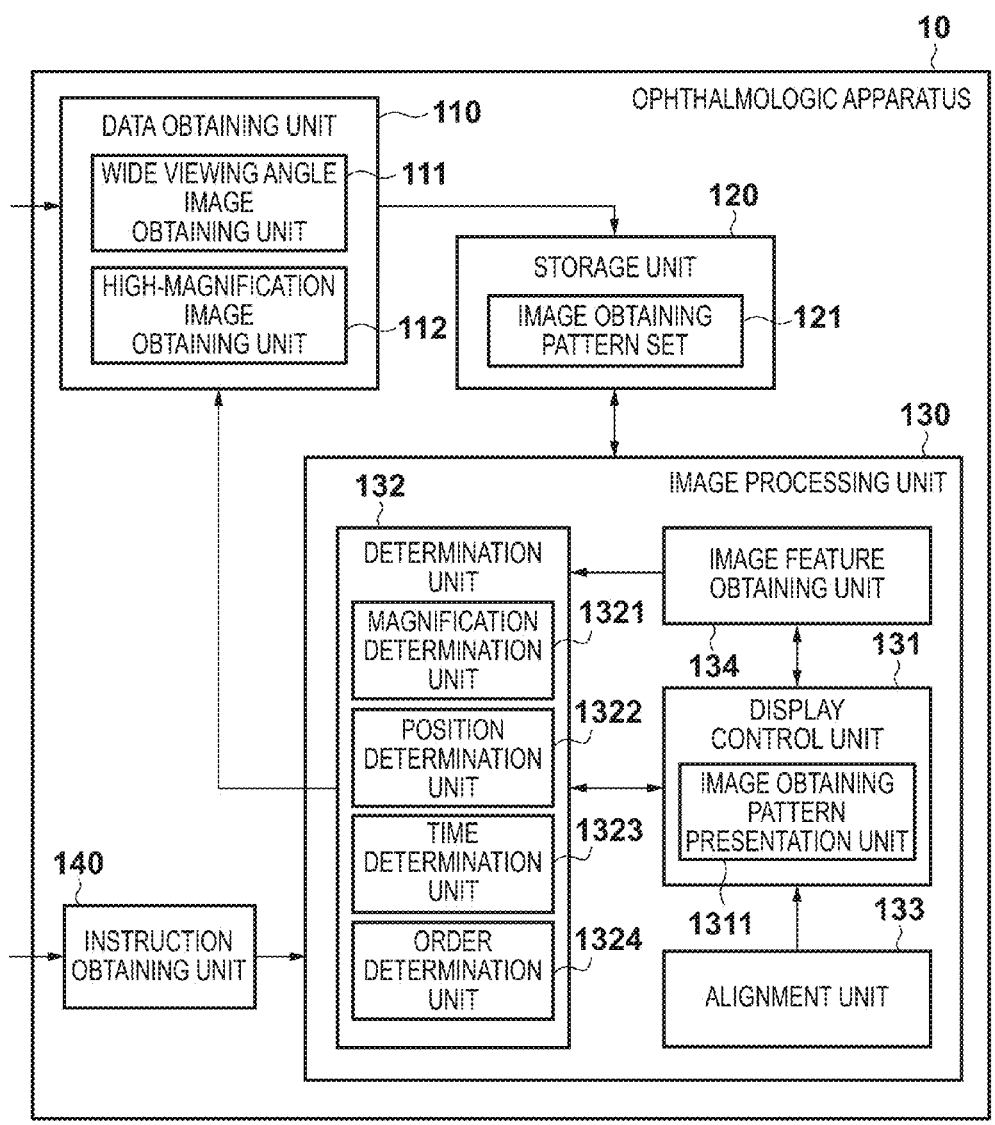

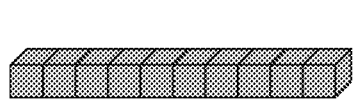
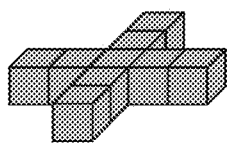
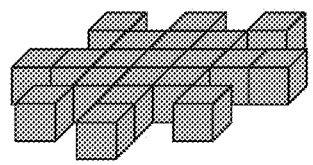
FIG. 15A  FIG. 15B  FIG. 15C
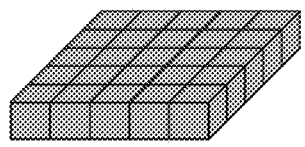
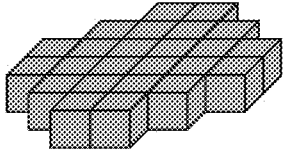
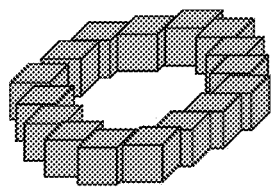
FIG. 15D  FIG. 15E  FIG. 15F
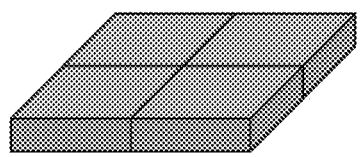
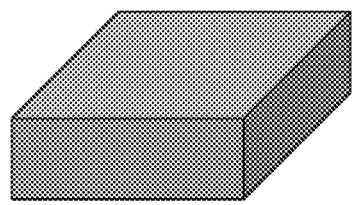
FIG. 15G  FIG. 15H
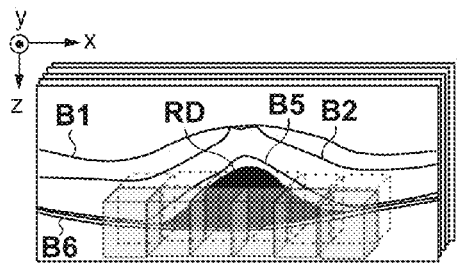
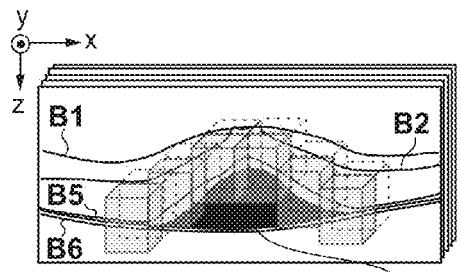
FIG. 15I  FIG. 15J

INFORMATION PROCESSING APPARATUS, INFORMATION PROCESSING METHOD AND COMPUTER READABLE STORAGE MEDIUM

This application claims the benefit of Japanese Patent Application No. 2013-111332, filed May 27, 2013, which is hereby incorporated by reference herein in its entirety.

BACKGROUND OF THE INVENTION

Field of the Invention

The present invention relates to an information processing apparatus, an information processing method, and a computer readable storage medium used for ophthalmologic diagnosis.

Description of the Related Art

To early diagnose life-style related diseases or diseases highly ranked as causes of blindness, eye examinations are widely conducted. As an ophthalmologic apparatus using the principle of a confocal scanning microscope, a Scanning Laser Ophthalmoscope (SLO) is known. The scanning laser ophthalmoscope raster-scans a laser beam serving as measurement light on a fundus, and quickly obtains a high-resolution planar image based on the intensity of return light. An apparatus for capturing such a planar image will be referred to as an SLO apparatus, and a captured planar image as an SLO image hereafter.

Recently, the SLO apparatus can obtain an SLO retinal image having an improved horizontal resolution by increasing the beam diameter of measurement light. However, as the beam diameter of measurement light increases, the S/N ratio and resolution of an SLO image decrease as a result of aberrations in the eye that is the subject of the examination. This results in a problem in obtaining an SLO retinal image. To solve this problem, an adaptive optics SLO apparatus has been developed, which includes an adaptive optics system configured to measure an aberration in an eye to be examined using a wave front sensor in real time and to correct an aberration of measurement light, or its return light, which takes place in the eye to be examined using a wave front correction device. This makes it possible to obtain an SLO image having a high horizontal resolution.

Such an SLO image having a high horizontal resolution can be obtained as a moving image. Various kinds of biological information can be measured using the moving image. For example, to noninvasively observe hemodynamics, a blood vessel of a retina is extracted from each frame, and the moving speed of blood cells in the capillary vessel, and the like, are measured. To evaluate the association with the visual performance using an SLO image, visual cells P are detected, and the density distribution or arrangement of the visual cells P is measured.

In fact, the viewing angle of one SLO image having a high horizontal resolution that the adaptive optics SLO apparatus can capture is typically small. For this reason, when the image capture target region is larger than the viewing angle of the SLO image having a high horizontal resolution, how to set an image capture region in the image capture target region becomes a problem. This will be described with reference to FIGS. 7A to 7G. FIG. 7A is a view schematically showing the section of an eye to be examined. FIGS. 7B to 7G are views showing examples of an SLO image or an image capture target region.

FIG. 7B is a view showing an example of an SLO image having a high horizontal resolution. In FIG. 7B, the visual cells P, a low-luminance region Q corresponding to the position of a capillary vessel, and a high-luminance region W corresponding to the position of a white blood cell are observed. To observe the visual cells P or to measure the distribution of the visual cells P, an SLO image as shown in FIG. 7B is captured by setting the focus position near an extraretinal layer (B5 in FIG. 7A).

On the other hand, blood vessels of the retina and branched capillary vessels run through intraretinal layers (B2 to B4 in FIG. 7A). Especially, in a diseased eye, the image capture target region is often larger than the viewing angle of one SLO image that the SLO apparatus can capture. FIGS. 7C and 7D show examples in which the image capture target region is larger than the viewing angle of an SLO image. FIG. 7C shows an example of the favorite site of a capillary vessel lesion (annular region surrounded by the broken line). FIG. 7D shows an example of a wide visual cell deficiency region (closed black region). In cases as shown in FIGS. 7C and 7D, if all image capture target regions are obtained under a high magnification, setting image capture conditions for many SLO images may be cumbersome, or an increase in the image capture time may make the burden heavy for the subject. The image capture target region includes both regions of great need to capture high-magnification images for diagnosis, and those of little need. It is, therefore, necessary to appropriately set image capture regions such that all regions where it is needed to obtain high-magnification images can be captured in an examination time that does not put a burden upon a subject.

In association with this, an arrangement that captures a plurality of adaptive optics SLO images by changing the image capture position and displays them as a panoramic image is described in Japanese Patent Laid-Open No. 2012-213513 as a technique concerning parameter setting for obtaining a plurality of high-magnification images.

However, when cells, tissues, or lesion regions to be observed or measured specifically distribute wider than a region covered by an image (high-magnification image DH) having a high horizontal resolution, the conventional arrangement has the following problems in efficiently capturing the region of the cells, or the like:

(i) the operator needs to individually designate the values of obtaining parameters (for example, obtaining position, viewing angle, pixel size, number of frames, and frame rate) of a plurality of high-magnification images DHj, inhibiting efficiently obtaining a plurality of images; and (ii) when an observation target region wider than the high-magnification image DH is captured using the same high-magnification image obtaining parameters, the number of high-magnification images (total number of frames) is enormous (several thousands to several tens of thousands), and it is, therefore, difficult to efficiently obtain the images.

In the arrangement of Japanese Patent Laid-Open No. 2012-213513 as well, the obtaining parameters of a number of high-magnification images are manually determined for each image. The operator is forced to perform cumbersome operations for setting the obtaining parameters.

SUMMARY OF THE INVENTION

The present invention has been made in consideration of the above-described problems, and provides a technique of efficiently and appropriately capturing, in a range wider than the viewing angle of a high-magnification image, tissues, cells, or lesion candidates whose distribution changes depending on an eye to be examined.

According to one aspect, the present invention provides an information processing apparatus for controlling, in one image capture region, image capture of a plurality of high-magnification images having a viewing angle smaller than the viewing angle of the image capture region, the apparatus comprising a presentation unit configured to present to an operator for selection a plurality of basic patterns each representing a distribution of positions at which to respectively capture high-magnification images, an adjustment unit configured to adjust, in accordance with an instruction of the operator, an image capture condition of the plurality of high-magnification images associated in advance with the basic pattern selected from the plurality of basic patterns, and a control unit configured to cause an image capture apparatus to capture the plurality of high-magnification images in the image capture region in accordance with the adjusted image capture condition.

Further features of the present invention will become apparent from the following description of embodiments (with reference to the attached drawings).

BRIEF DESCRIPTION OF THE DRAWINGS

FIGS. 6A to 6M are views for explaining image obtaining patterns;

FIGS. 7A to 7G are views for explaining contents of image processing;

FIG. 8 is a flowchart showing details of high-magnification image obtaining processing;

FIG. 9 is a flowchart showing details of image display processing;

FIG. 10 is a block diagram showing an example of the functional arrangement of an ophthalmologic apparatus 10;

FIG. 11 is a flowchart showing details of high-magnification image obtaining processing;

FIG. 13 is a block diagram showing an example of the functional arrangement of an ophthalmologic apparatus 10;

FIGS. 15A to 15J are views for explaining image obtaining patterns; and

DESCRIPTION OF THE EMBODIMENTS

The embodiments of the present invention will now be described in detail with reference to the accompanying drawings.

First Embodiment

When obtaining a plurality of high-magnification adaptive optics SLO images, an ophthalmologic apparatus as an information processing apparatus according to this embodiment presents basic patterns of parameters associated with image capture conditions prepared in advance for obtaining a plurality of high-magnification images by an operator (user), and causes the operator to select a pattern. Next, the ophthalmologic apparatus causes the operator to adjust the image obtaining parameters as needed in accordance with the lesion shape, and determines obtaining parameter values concerning a plurality of high-magnification images in accordance with the contents of the adjustment. An example will be described below in which the operator selects a basic pattern for obtaining a plurality of images in a disc-shaped pattern for a wide visual cell deficiency region of a macular portion, and determines the obtaining position, the viewing angle, the pixel size, the number of frames, the frame rate, and the in-focus position of each high-magnification image.

(Overall Arrangement)

Figure 1A:
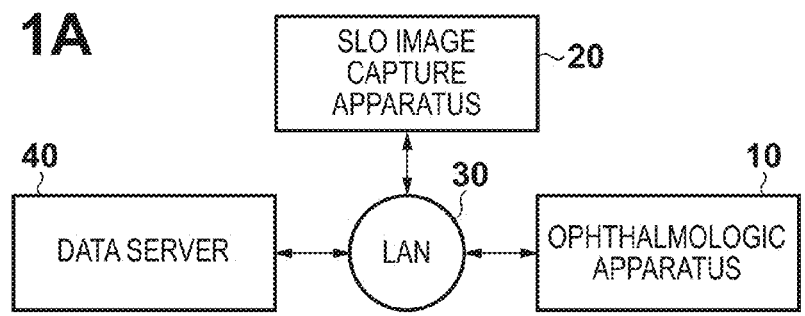
FIGS. 1A to 1C are block diagrams showing examples of arrangements of a system including an ophthalmologic apparatus 10.

FIG. 1A is a block diagram showing the arrangement of a system including an ophthalmologic apparatus 10 according to this embodiment. As shown in FIG. 1A, the ophthalmologic apparatus 10 is connected to an SLO image capture apparatus 20 serving as an image capture apparatus and a data server 40 via a LAN (Local Area Network) 30 formed from an optical fiber, USB, IEEE 1394, and the like. Note that the connection form of these apparatuses is not limited to the example shown in FIG. 1A. For example, these apparatuses may be connected via an external network such as the Internet. Alternatively, the ophthalmologic apparatus 10 may be connected directly to the SLO image capture apparatus 20.

The SLO image capture apparatus 20 captures (shoots) a wide viewing angle image $D_L$ or a high-magnification image $D_H$ of a fundus portion. The SLO image capture apparatus 20 transmits the wide viewing angle image $D_L$ or high-magnification image $D_H$, and information of fixation mark positions $F_L$ and $F_H$ used at the time of image capture to the ophthalmologic apparatus 10 and the data server 40.

Note that when the images of respective magnifications are obtained at different image capture positions, the obtained images are represented by $D_{Li}$ and $D_{Hj}$. More specifically, i and j are variables representing image capture positions, which are set as i=1, 2, . . . , imax, and j=1, 2, . . . , jmax. When high-magnification images are obtained under a plurality of different magnifications, they are represented by $D_{1j}, D_{2k}, \ldots$ in descending order of magnifications. The image $D_{1j}$ of the highest magnification will be referred to as a high-magnification image, and the images $D_{2k}, \ldots$ as intermediate-magnification images.

The data server 40 holds image capture condition data, image features of an eye, normal values associated with the distribution of image features of an eye, and the like. As the image capture condition data, the data server 40 stores the wide viewing angle images DL and the high-magnification images DH of an eye to be examined and the fixation mark positions FL and FH used at the time of image capture, which are output from the SLO image capture apparatus 20, and the image features of the eye output from the ophthalmologic apparatus 10. In this embodiment, image features associated with visual cells P, capillary vessels Q, blood cells W, blood vessels of a retina, and retinal layer boundaries are handled as the image features of an eye. In response to a request from the ophthalmologic apparatus 10, the data server 40 transmits the wide viewing angle images $D_L$, the high-magnification images $D_H$, the image features of the eye, and normal value data of the image features to the ophthalmologic apparatus 10.

(Ophthalmologic Apparatus)

Figure 2:
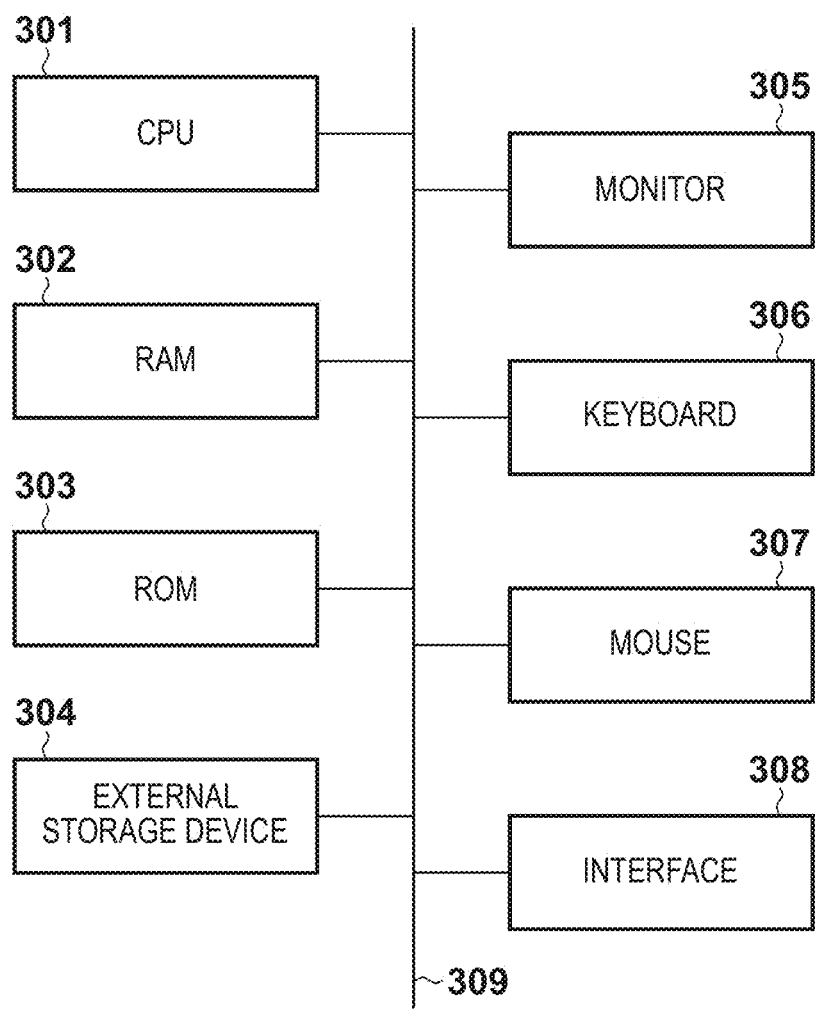
FIG. 2 is a block diagram showing an example of the hardware arrangement of the ophthalmologic apparatus 10.

The ophthalmologic apparatus 10 is implemented by an information processing apparatus such as a built-in system, a personal computer (PC), or a tablet terminal. The hardware arrangement of the ophthalmologic apparatus 10 will be described with reference to FIG. 2. Referring to FIG. 2, a CPU 301 is a central processing unit, and controls the operation of the entire ophthalmologic apparatus in cooperation with other constituent elements based on a computer program such as an OS (Operating System) or an application program. A RAM 302 is a writable memory, and functions as the work area of the CPU 301, or the like. A ROM 303 is a read only memory, and stores programs such as a basic I/O program and data to be used in basic processing. An external storage device 304 is a device functioning as a mass memory, and is implemented by a hard disk drive or a semiconductor memory. A monitor 305 is a display device serving as a display means for displaying a command input from a keyboard 306 or a pointing device 307, an output of the ophthalmologic apparatus 10 responding to it, and the like. The keyboard 306 and the pointing device 307 are devices that accept an instruction or a command input from the operator. An interface 308 is a device that relays data exchange with an external apparatus.

A control program that implements an image processing function according to this embodiment and data to be used when executing the control program are stored in the external storage device 304. The control program and data are loaded to the RAM 302, as needed, via a bus 309 under the control of the CPU 301, and executed by the CPU 301 so as to function as units to be described below.

Figure 3:
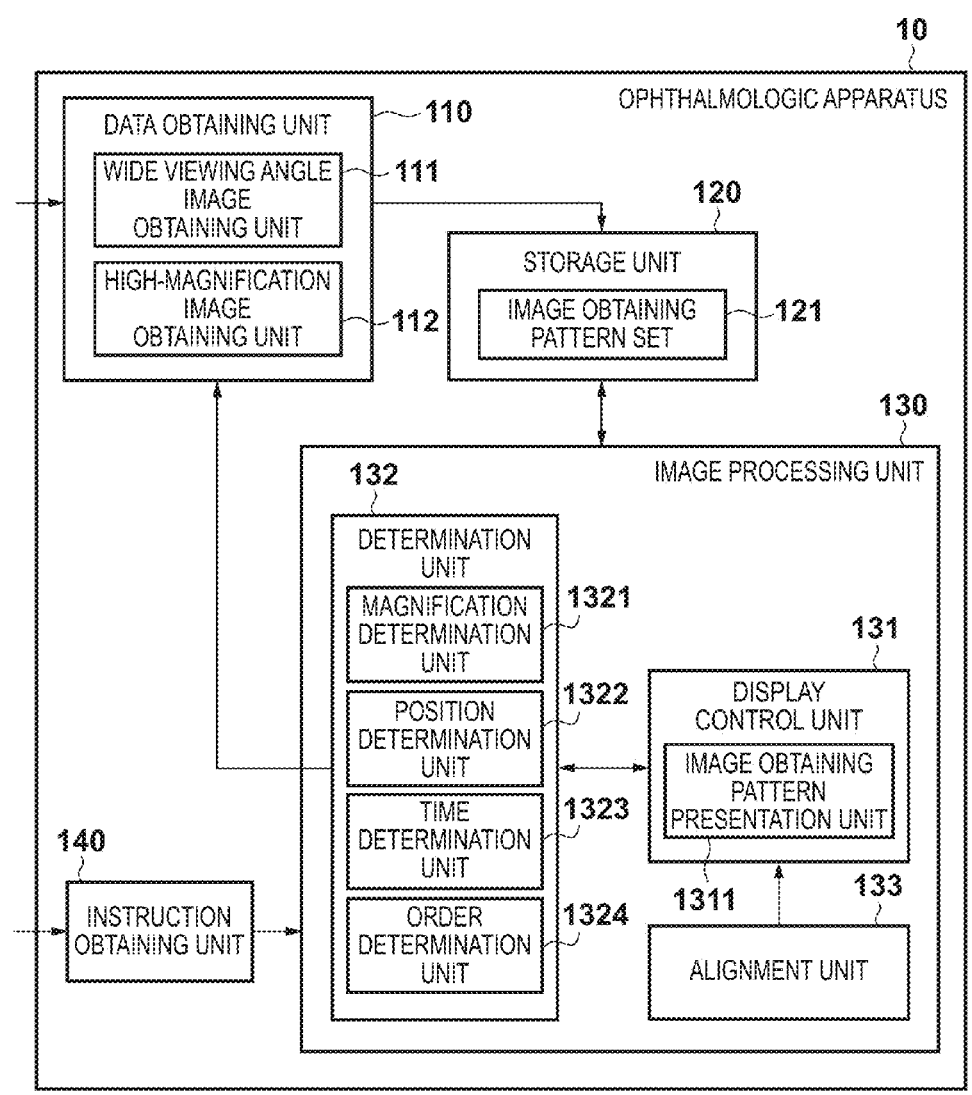
FIG. 3 is a block diagram showing an example of the functional arrangement of the ophthalmologic apparatus 10.

The functional arrangement of the ophthalmologic apparatus 10 according to this embodiment will be described next with reference to FIG. 3. FIG. 3 is a block diagram showing the functional arrangement of the ophthalmologic apparatus 10. As shown in FIG. 3, the ophthalmologic apparatus 10 includes a data obtaining unit 110, a storage unit 120, an image processing unit 130, and an instruction obtaining unit 140.

The data obtaining unit 110 is a functional block that obtains data such as image data and image capture condition data. The data obtaining unit 110 includes a wide viewing angle image obtaining unit 111 that obtains a wide viewing angle image, and a high-magnification image obtaining unit 112 that obtains a high-magnification image. The storage unit 120 is a functional block that holds data obtained by the data obtaining unit 110 and an image obtaining pattern set 121. The image obtaining pattern set 121 is a set of basic setting patterns (to be referred to as "image obtaining patterns" hereafter) associated with parameters when obtaining a plurality of high-magnification images.

The image processing unit 130 is a functional block that performs processing such as determination of image capture conditions, setting of the image capture conditions, and display of captured images. The image processing unit 130 includes a display control unit 131 that performs captured image display control, and the like, a determination unit 132 that determines image capture conditions, and an alignment unit 133 that aligns an image capture region based on the image capture conditions. The display control unit 131 includes an image obtaining pattern presentation unit 1311 that displays an image obtaining pattern on the monitor and presents it to the operator. The determination unit 132 includes a magnification determination unit 1321 that determines the magnification for image capture, a position determination unit 1322 that determines an image capture position, a time determination unit 1323 that determines the timing of image capture, and the like, and an order determination unit 1324 that determines the order of image capture.

(SLO Image Capture Apparatus)

Figure 4:
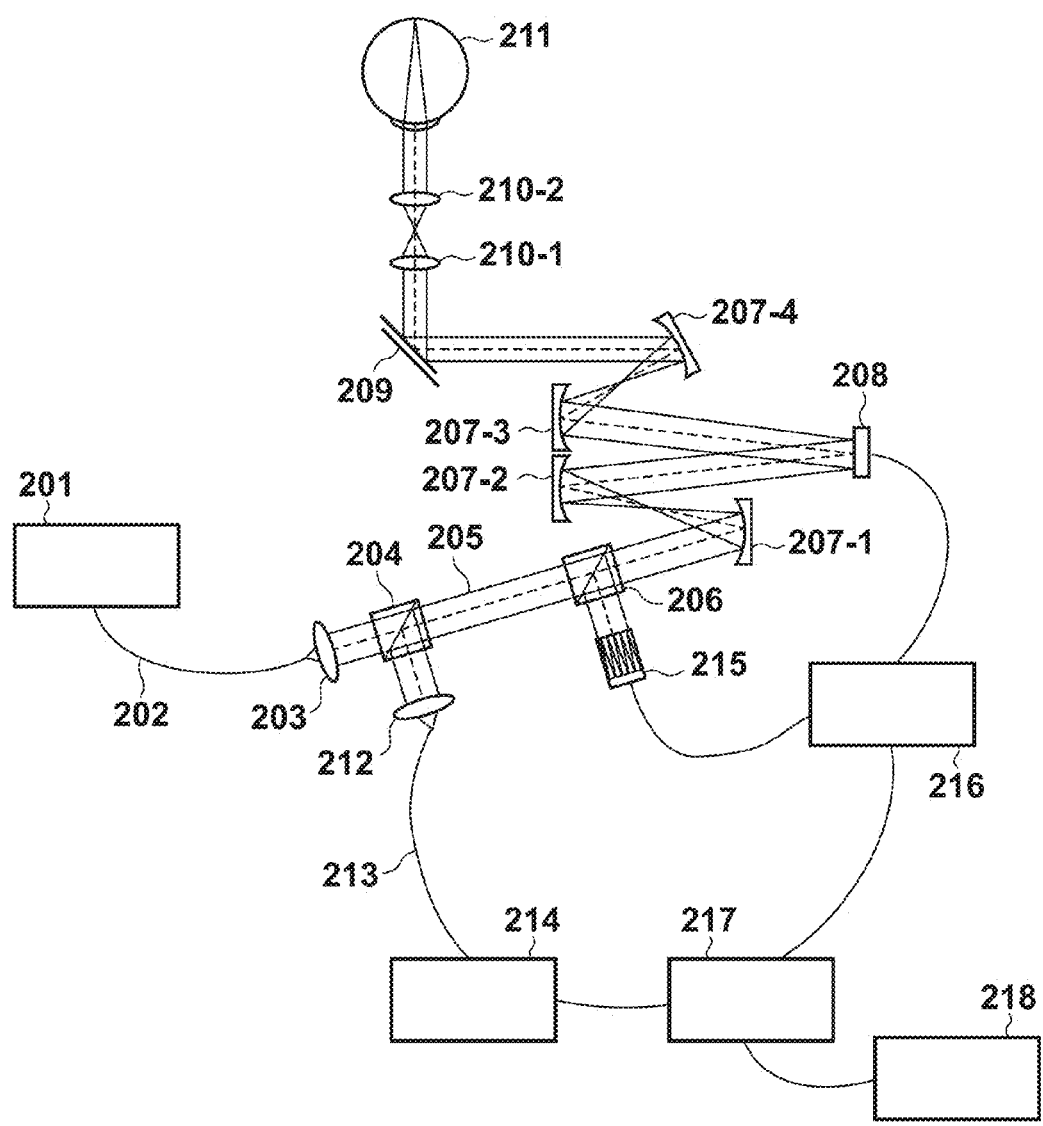
FIG. 4 is a view for explaining the overall arrangement of an SLO image capture apparatus 20.

An example of the arrangement of the SLO image capture apparatus 20, including an adaptive optics system, will be described next with reference to FIG. 4. Note that the arrangement of the SLO image capture apparatus to be described below is merely an example, and the SLO image capture apparatus can be constituted using any image capture apparatus as long as it can obtain a high-magnification image.

Reference numeral 201 denotes a light source. FIG. 4 shows an example in which the light source 201 is implemented by an SLD (Super Luminescent Diode). In this embodiment, both a light source used to capture a fundus image and that used to measure a wave front are implemented by the light source 201. However, separate light sources may be used, and light beams may be combined halfway through the optical path.

Light emitted by the light source 201 passes through a single-mode optical fiber 202 and exits from a collimator 203 as parallel measurement light 205. The measurement light 205 that has exited passes through a light division unit 204 formed from a beam splitter and is guided to the adaptive optics system.

The adaptive optics system includes a light division unit 206, a wave front sensor 215, a wave front correction device 208, and reflecting mirrors 207-1 to 207-4 configured to guide light to them. The reflecting mirrors 207-1 to 207-4 are disposed such that at least the pupil of an eye becomes optically conjugate with the wave front sensor 215 and the wave front correction device 208. In this embodiment, a beam splitter is used as the light division unit 206. In this embodiment, a spatial phase modulator using a liquid crystal element is used as the wave front correction device 208. Note that a deformable mirror may be used as the wave front correction device. The light that has passed through the adaptive optics system is one- or two-dimensionally scanned by a scanning optical system 209.

In this embodiment, two galvanoscanners are used for main scanning (horizontal direction of fundus) and sub-scanning (vertical direction of fundus) as the scanning optical system 209. For faster image capture, a resonant scanner may be used on the main scanning side of the scanning optical system 209.

The measurement light 205 scanned by the scanning optical system 209 irradiates an eyeball 211 through eyepieces 210-1 and 210-2. The measurement light 205 that has irradiated the eyeball 211 is reflected or scattered by the fundus. Optimum irradiation can be performed in accordance with the diopter scale of the eyeball 211 by adjusting the positions of the eyepieces 210-1 and 210-2. Note that although a lens is as an eyepiece portion here, it may be formed from a spherical mirror, or the like.

Reflected/scattered light (return light) reflected or scattered by the retina of the eyeball 211 travels back through the same path as that of the incident light. The light is partially reflected by the light division unit 206 toward the wave front sensor 215 and used to measure the wave front of the light beam. The wave front sensor 215 is connected to an adaptive optics control unit 216 and transmits the received wave front to the adaptive optics control unit 216. The wave front correction device 208 is also connected to the adaptive optics control unit 216 and performs modulation instructed by the adaptive optics control unit 216. The adaptive optics control unit 216 calculates, based on the wave front measured by the wave front sensor 215, a modulation amount (correction amount) that corrects the wave front reaching the wave front correction device 208 to a wave front free from aberrations, and instructs the wave front correction device 208 to modulate the wave front so. Note that the wave front measurement and the instruction to the wave front correction device 208 are repetitively processed, and feedback control is performed so as to always obtain an optimum wave front.

The reflected/scattered light that has passed through the light division unit 206 is partially reflected by the light division unit 204 and guided to a light intensity sensor 214 through a collimator 212 and an optical fiber 213. The light intensity sensor 214 converts the light into an electrical signal. A control unit 217 constructs an image as a fundus image and displays it on a display 218. Note that in the arrangement shown in FIG. 4, when the swing angle of the scanning optical system is increased, and the adaptive optics control unit 216 instructs not to correct aberrations, the SLO image capture apparatus 20 can operate as a normal SLO apparatus and capture a wide viewing angle SLO image (wide viewing angle image $D_L$).

(Processing Procedure)

Figure 5:
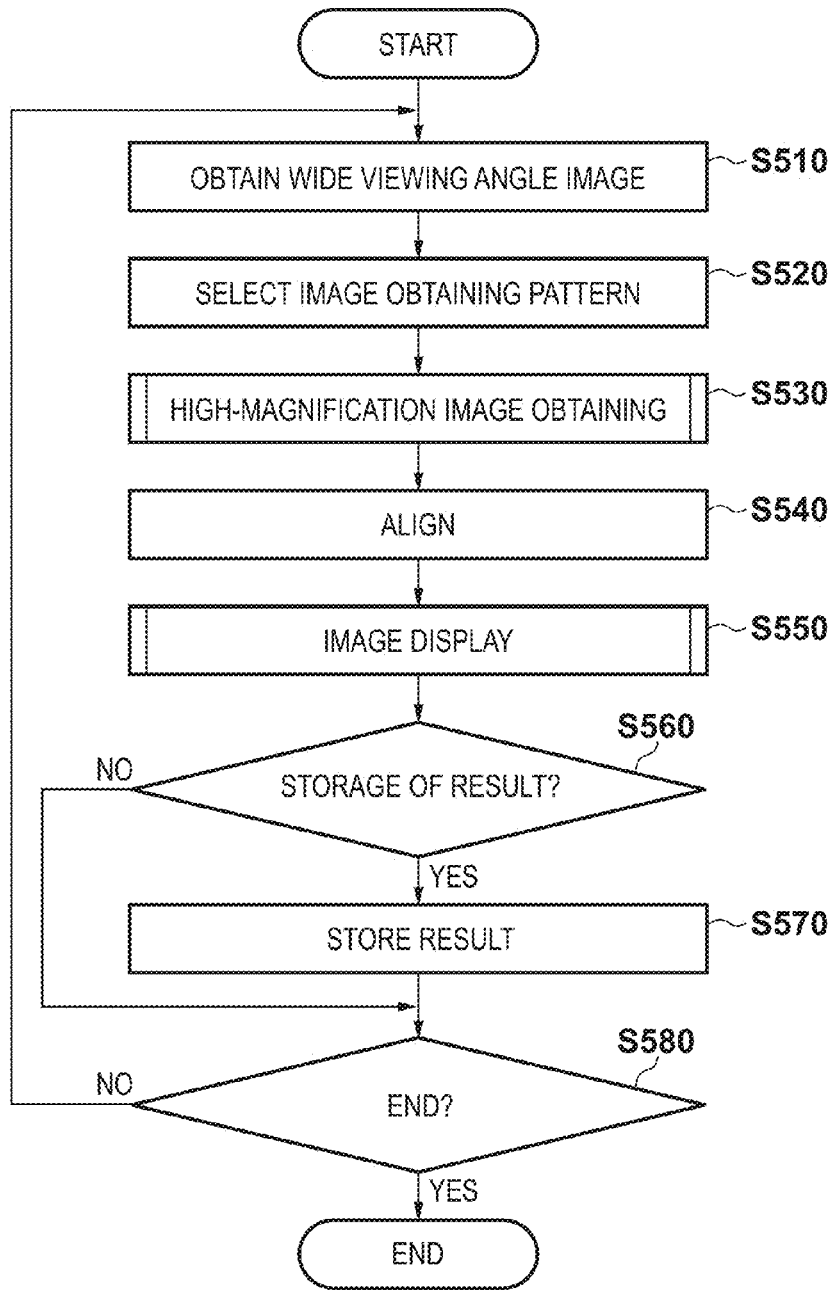
FIG. 5 is a flowchart of processing executed by the ophthalmologic apparatus 10.

Specific contents of processing executed by the ophthalmologic apparatus 10 will be described in detail in association with the roles of the functional blocks. FIG. 5 is a flowchart showing the processing procedure executed by the ophthalmologic apparatus 10. The following processes are executed under the control of the CPU 301.

<Step S510>

The wide viewing angle image obtaining unit 111 requests the SLO image capture apparatus 20 to obtain the wide viewing angle image $D_L$ and the fixation mark position $F_L$. In this embodiment, an example will be explained in which the wide viewing angle image $D_L$ is obtained by setting the fixation mark position $F_L$ in the fovea centralis (the center-of-gravity position of the avascular region) of a macular portion. Note that the image capture position setting method is not limited to this, and the image capture position may be set at another arbitrary position.

In response to the obtaining request from the wide viewing angle image obtaining unit 111, the SLO image capture apparatus 20 obtains the wide viewing angle image $D_L$ and the fixation mark position $F_L$, and transmits them to the wide viewing angle image obtaining unit 111. The wide viewing angle image obtaining unit 111 receives the wide viewing angle image $D_L$ and the fixation mark position $F_L$ from the SLO image capture apparatus 20 via the LAN 30. The wide viewing angle image obtaining unit 111 stores the received wide viewing angle image $D_L$ and fixation mark position $F_L$ in the storage unit 120. Note that in the example of this embodiment, the wide viewing angle image $D_L$ is a moving image whose frames have already been aligned.

<Step S520>

The image obtaining pattern presentation unit 1311 obtains at least one type of image obtaining pattern (basic setting pattern associated with parameters when obtaining a plurality of high-magnification images) from the storage unit 120 and selectively displays it on the monitor 305. An arbitrary pattern can be presented as the image obtaining pattern. In the example of this embodiment, a case when basic patterns as shown in FIGS. 6A to 6F are presented will be described. FIG. 6A shows a linear pattern, FIG. 6B shows a cruciform pattern, FIG. 6C shows a radial pattern, FIG. 6D shows a rectangular pattern, FIG. 6E shows a disc-shaped pattern, and FIG. 6F shows an annular pattern.

The instruction obtaining unit 140 externally obtains an instruction about selection of an image obtaining pattern desired by the operator. This instruction is input by the operator via, for example, the keyboard 306 or the pointing device 307. Alternatively, if the monitor 305 includes a liquid crystal touch panel, the instruction may be input via the touch panel. In the example of this embodiment, since the observation target is a disc-shaped visual cell deficiency region as shown in FIG. 7D, the disc-shaped image obtaining pattern shown in FIG. 6E is selected.

Note that, not only an image obtaining pattern including only high-magnification images under one type of magnification as shown in FIGS. 6A to 6F, but also an image obtaining pattern formed by combining images of a plurality of magnifications can be presented. For example, as shown in FIG. 6G, not only the high-magnification images $D_{1j}$, but also the intermediate-magnification images $D_{2k}$ can be defined to be included in an obtaining pattern. An obtaining pattern including, not only high-magnification images, but also intermediate-magnification images will be referred to as a "multiple magnification image obtaining pattern" hereafter. Such an image obtaining pattern is suitable when decreasing the number of obtained images or when performing more accurate alignment with the wide viewing angle image $D_L$. Note that in the multiple magnification image obtaining pattern, image obtaining patterns formed by high-magnification images and intermediate-magnification images can have the same shape or different shapes on the magnification basis. For example, the intermediate-magnification images $D_{2k}$ of a lower magnification may be obtained in a rectangular pattern, and the high-magnification images $D_{1j}$ may be obtained in a disc-shaped pattern. When the image obtaining pattern changes between different magnifications, information of the type of image obtaining pattern of each magnification is also obtained in this step. Note that FIG. 6G shows a case when both the image obtaining pattern formed by the high-magnification images $D_{1j}$ and that formed by the intermediate-magnification images $D_{2k}$ have the same cruciform shape.

Figure 6G:
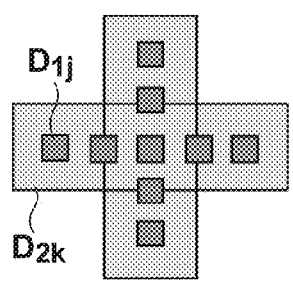
Figure 6H:
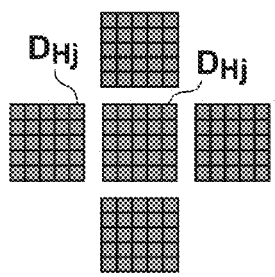
Figure 6I:
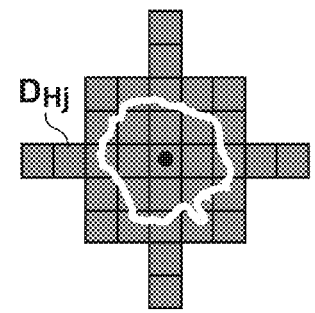

A pattern in which a plurality of basic patterns are arranged at different positions (to be referred to as a "multiple arrangement image obtaining pattern" hereafter), as shown in FIG. 6H, may be presented. FIG. 6H illustrates a pattern in which a plurality of rectangular image obtaining patterns are arranged. This pattern is suitable when a plurality of lesions exist or when comparing the form or dynamics of an observation target between portions. Note that the multiple arrangement image obtaining pattern also includes a case when images are obtained by changing the in-focus position between basic patterns. An image obtaining pattern (to be referred to as a "composite image obtaining pattern" hereafter) defined by a combination of basic patterns, as shown in FIG. 6I, may be presented. The composite image obtaining pattern is suitable when efficiently obtaining images for different purposes by one examination. For example, the pattern in FIG. 6I is suitable for both a case when the shape of an avascular region (a closed region indicated by a white line in FIG. 6I) at the fovea centralis (the center-of-gravity position of the avascular region) indicated by a full circle in FIG. 6I is measured (rectangular pattern) and a case when the visual cell density is measured every predetermined distance from the fovea centralis (cruciform pattern).

<Step S530>

The determination unit 132 determines the obtaining parameters of a plurality of high-magnification images by setting the obtaining parameters of a plurality of images included in the image obtaining pattern selected in step S520 as initial values, and causing the operator to adjust the image obtaining parameters as needed, and images are obtained. The processing (to be referred to as "high-magnification image obtaining processing" hereafter) of this step will be described later in detail with reference to the flowchart of FIG. 8.

<Step S540>

The alignment unit 133 aligns the wide viewing angle image $D_L$ and the high-magnification images $D_H$, and obtains the relative positions of the high-magnification images $D_H$ on the wide viewing angle image $D_L$. Alignment means automatically judging the positional relationship between the wide viewing angle image $D_L$ and the high-magnification images $D_H$ and setting the positions of the high-magnification images $D_H$ at the corresponding positions of the wide viewing angle image $D_L$. Note that the wide viewing angle image $D_L$ is an image given in advance and having a magnification lower than the high-magnification images to represent the entire image capture region. If an overlap region exists between the high-magnification images $D_{Hj}$, first, the degree of similarity between the images is calculated concerning the overlap region, and the positions of the high-magnification images $D_{Hj}$ are aligned with a position where the degree of similarity between the images is maximum. Next, if high-magnification images having different resolutions are obtained in step S530, alignment is performed sequentially from an image of a lower magnification. For example, when the high-magnification image $D_{1j}$ and the intermediate-magnification image $D_{2k}$ are obtained as the high-magnification images $D_H$, alignment is performed first between the wide viewing angle image $D_L$ and the intermediate-magnification image $D_{2k}$. Then, alignment is performed between the intermediate-magnification image $D_{2k}$ and the high-magnification image $D_{1j}$. If the high-magnification images have only one type of resolution, only alignment between the high-magnification images $D_H$ and the wide viewing angle image $D_L$ is performed, as a matter of course.

Note that the alignment unit 133 obtains the fixation mark position $F_H$ used when capturing the high-magnification images $D_H$ from the storage unit 120, and sets it as the initial point for an alignment parameter search in alignment between the wide viewing angle image $D_L$ and the high-magnification images $D_H$. As the degree of similarity between images or the coordinate transformation method, an arbitrary known method is usable. In this embodiment, alignment is performed using a correlation coefficient as the degree of similarity between images and affine transformation as the coordinate transformation method.

<Step S550>

The display control unit 131 displays the high-magnification images $D_H$ on the wide viewing angle image $D_L$ based on the alignment parameter values obtained in step S540. The processing (to be referred to as "image display processing" hereafter) of this step will be described later in detail with reference to the flowchart of FIG. 9.

<Step S560>

The instruction obtaining unit 140 externally obtains an instruction of whether to store the wide viewing angle image $D_L$, the high-magnification images $D_H$, the fixation mark positions $F_L$ and $F_H$, and the alignment parameter values obtained in step S540 in the data server 40. This instruction is input by the operator via, for example, the keyboard 306 or the pointing device 307. When storage is instructed (YES in step S560), the process advances to step S570. When storage is not instructed (NO in step S560), the process advances to step S580.

<Step S570>

The image processing unit 130 associates the examination date/time, information for identifying the eye to be examined, the wide viewing angle image $D_L$, the high-magnification images $D_H$, the fixation mark positions $F_L$ and $F_H$, and the alignment parameter values with each other, and transmits them to the data server 40.

<Step S580>

The instruction obtaining unit 140 externally obtains an instruction of whether to end the processing of the wide viewing angle image $D_L$ and the high-magnification images $D_H$ by the ophthalmologic apparatus 10. This instruction is input by the operator via, for example, the keyboard 306 or the pointing device 307. Upon obtaining an instruction to end the processing (YES in step S580), the processing ends. Upon obtaining an instruction to continue the processing (NO in step S580), the process returns to step S510 to perform processing for the next eye to be examined or the same eye.

(High-Magnification Image Obtaining Processing)

Details of high-magnification image obtaining processing executed in step S530 will be described next with reference to the flowchart of FIG. 8.

<Step S810>

The determination unit 132 obtains, from the storage unit 120, the type of an image obtaining pattern selected via the instruction obtaining unit 140 and the obtaining parameter values of each high-magnification image $D_H$ of the pattern. More specifically, out of the obtaining parameters of each high-magnification image held by the selected image obtaining pattern, the following parameter values are input as initial values. That is, the determination unit 132 inputs the values of the number of magnifications, the viewing angle, and the pixel size to the magnification determination unit 1321, the obtaining position and in-focus position to the position determination unit 1322, the number of frames, the frame rate, and the repetitive obtaining count to the time determination unit 1323, and the obtaining order to the order determination unit 1324 as initial values.

<Step S820>

The determination unit 132 obtains, via the instruction obtaining unit 140, constraint conditions associated with the set values of the obtaining parameters of each high-magnification image $D_{Hj}$ included in the selected image obtaining pattern. The constraint conditions define ranges that the image capture conditions can take. The operator can designate/set the constraint conditions associated with an arbitrary image obtaining pattern. In the example of this embodiment, a case will be described where the operator can set the following four constraint conditions:

(a) total image obtaining time;
(b) magnification type (number of magnifications, viewing angle, and pixel size);
(c) in-focus position; and
(d) overlap region between adjacent high-magnification images.

In this case, (a) is a constraint condition associated with an allowed time that the eye to be examined can endure;
(b) is a constraint condition associated with the magnitude of an image feature expected to be obtained at an image capture position;
(c) is a constraint condition associated with the depth (z-axis) direction position where the observation target exists; and
(d) an allowable fixation disparity amount of the eye to be examined.

In this embodiment, an example will be explained in which
(a) 15 min;
(b) 1 and 300 [µm]×300 [µm], and 1 [µm/pixel]×1 [µm/pixel];
(c) visual cell layer; and
(d) 20% of high-magnification image area
are set.

<Step S830>

The magnification determination unit 1321 determines the magnification type (number of magnifications, viewing angle, and pixel size) of the high-magnification images $D_H$. Additionally, the position determination unit 1322 determines the obtaining position and the in-focus position of each high-magnification image $D_{Hj}$.

In this embodiment, the viewing angle, the pixel size, and the in-focus position are fixed values due to the constraint conditions obtained in step S820, but the obtaining position of each high-magnification image $D_{Hj}$ is a variable parameter. Hence, the operator first designates the position of a point (representative point) that represents the image obtaining pattern on the fundus. In this embodiment, the representative point is a central point C in FIG. 6E and is set at the fovea centralis of the eye to be examined. Next, the operator enlarges or reduces the size of the entire image obtaining pattern, thereby increasing or decreasing the number of high-magnification image obtaining positions while maintaining the size of the overlap region between high-magnification images, and determining the obtaining position of each high-magnification image $D_{Hj}$. In this embodiment, when the operator moves the position of (one) high-magnification image located at an end of the image obtaining pattern out of the disc, the size of the entire image obtaining pattern is enlarged, and the obtaining positions of the high-magnification images $D_{Hj}$ indicated by white line rectangular regions in FIG. 7G are determined.

Note that the representative point is not limited to the central point of the image obtaining pattern. For example, it may be the position of a specific high-magnification image included in the image obtaining pattern. In a multiple magnification image obtaining pattern as shown in FIG. 6G, the sizes of the image obtaining patterns of all magnifications may be enlarged or reduced at once, or the image obtaining pattern size may be changed for each magnification.

In a multiple arrangement image obtained pattern as shown in FIG. 6H as well, the sizes or arrangement intervals of all image obtained patterns may be changed at once. The size or arrangement interval of the image obtained pattern may change between the basic patterns. In a composite image obtaining pattern as shown in FIG. 6I as well, the sizes of patterns of all types may be changed at once, or the image obtaining pattern size may change between the image obtaining pattern types.

<Step S840>

Figure 6J:
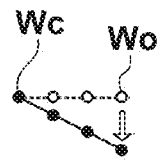

The time determination unit 1323 determines the number of frames, the frame rate, and the repetitive obtaining count of the high-magnification images. In the example of this embodiment, the frame rate and the repetitive obtaining count are fixed to 32 [frames/sec] and 1, respectively, and the number of frames is a variable parameter. As for a variable parameter value changing method, the variable parameter value can be designated using an arbitrary known user interface (to be abbreviated as "UI" hereafter). In the example of this embodiment, the operator operates a parameter value (weight) changing UI as shown in FIG. 6J, thereby efficiently changing the parameter value. This is a UI configured to adjust the weight in the radial direction associated with the number of frames of each high-magnification image $D_{Hj}$. In FIG. 6J, We represents a central weight of the arranged disc-shaped image obtaining pattern (FIG. 7G), and Wo represents an outer weight. When the outer weight Wo is lowered, the number of frames of each high-magnification image $D_{Hj}$ is automatically determined so as to become smaller stepwise outward from the pattern center.

Figure 6K:
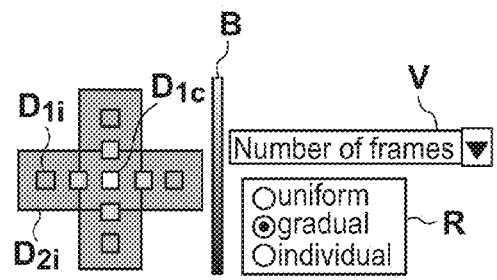

In a multiple magnification pattern as shown in FIG. 6G, a parameter value (or weight) adjustment UI as shown in FIG. 6K is usable. Parameter value adjustment is done in accordance with the following procedures (i) to (iv):

(i) select an adjustment target variable parameter from a variable parameter list V;

(ii) select, from an adjustment map, a target magnification and a target image for which parameter value adjustment is to be done;

(iii) select a parameter value changing (weighting) method R for a plurality of images under the selected magnification; and (iv) determine the parameter value (weight) for the selected image on the parameter value changing UI (B in FIG. 6K).

Note that in (i), the adjustment map shown in FIG. 6K is displayed for each type of selected variable parameter. Concerning (ii), FIG. 6K illustrates a case when the target magnification is $D_1$, and an image $D_{1c}$ at the center is selected as the adjustment target image.

For (iii), FIG. 6K illustrates an example in which the parameter value setting (weighting) method R for the images is selected from setting the same value for the plurality of images of the same magnification (uniform), changing the parameter value stepwise (gradual), and changing the parameter value between individual designated images (individual). In the example shown in FIG. 6K, changing the parameter value stepwise (gradual) is selected.

Concerning (iv), FIG. 6K illustrates a case when the operator designates the maximum value (white) on a color bar B, thereby automatically changing the parameter values of the images of the same magnification as that of the selected target image $D_{1c}$ such that the parameter value increases stepwise toward the selected image $D_{1c}$.

Note that in FIG. 6K, the color bar B is used as the parameter value changing UI, and the parameter values are expressed by a gray scale. However, the present invention is not limited to this. For example, the parameter value changing UI may be a slider or a list box (of numerical values). The parameter values may be displayed as numerical values (parameter values themselves or weights) or by color. Alternatively, the parameter values may be displayed using both numerical values and the gray scale (color).

Figure 6L:
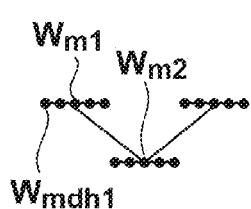
Figure 6M:
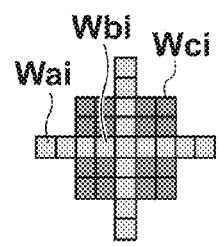

In a multiple arrangement pattern as shown in FIG. 6H, both a weight (for example, Wm1*dhi* in FIG. 6L) in each pattern and weights (Wm1 and Wm2) between the patterns are adjusted, as shown in FIG. 6L. In a composite image obtaining pattern as shown in FIG. 6M, parameter values (Wai and Wci) in the respective patterns and a parameter value (Wbi) in the image common to both patterns are set. The adjustment procedure is almost the same as that for the multiple magnification image obtaining pattern in FIG. 6K. More specifically, the above-described procedure (iii) is only replaced by a procedure of selecting the parameter value changing (weighting) method R for a plurality of images not under the selected magnification, but in a selected pattern or a common region.

<Step S850>

The order determination unit 1324 determines the obtaining order of the high-magnification images $D_{Hj}$. In this embodiment, repetitive processing is performed by setting, out of (i) to (iv) to be described below, (i) as the innermost loop (highest priority), (ii) as the second inner loop, (iii) as the third inner loop, and (iv) as the outermost loop (lowest priority). More specifically, the following procedures are executed by setting the obtaining start position at the most important position for observation (in this embodiment, fovea centralis) and the obtaining magnification to the lowest magnification:

(i) obtain images of the same arrangement pattern, same obtaining magnification, and same image obtaining position as many as the repetitive obtaining count;
(ii) move an image of the same arrangement pattern and same obtaining magnification to an adjacent image obtaining position and obtain images again in accordance with the same procedure as (i);
(iii) when (ii) has ended, increase the value of the obtaining magnification, execute the operation (ii) again, and repeat the same operation as many times as the number of magnifications; and
(iv) when (iii) has ended, execute the operation (iii) in another arrangement, and repeat the operation until images are obtained in all arrangements.

Note that in the example of this embodiment, no repetitive obtaining is performed in (i) (the obtaining count is only 1), and the processing (iv) is omitted because the image obtaining pattern is not a multiple arrangement pattern as shown in FIG. 6H. The movement to an adjacent image in (ii) can be done in an arbitrary direction. In this embodiment, the image is moved spirally from the fovea centralis because the influence on visual performance increases, and the importance in observation becomes high as the distance to the fovea centralis shortens.

With the processes of steps S830 to S850, the operator can easily change the image obtaining parameters representing the image capture conditions for the high-magnification images.

<Step S860>

The high-magnification image obtaining unit 112 requests the SLO image capture apparatus 20 to obtain the plurality of high-magnification images $D_{Hj}$ and fixation mark positions $F_{Hj}$ using the image obtaining parameters designated by the determination unit 132. The SLO image capture apparatus 20 obtains the high-magnification images $D_{Hj}$ and the fixation mark positions $F_{Hj}$ and transmits them in response to the obtaining request. The high-magnification image obtaining unit 112 receives the high-magnification images $D_{Hj}$ and the fixation mark positions $F_{Hj}$ from the SLO image capture apparatus 20 via the LAN 30. The high-magnification image obtaining unit 112 stores the received high-magnification images $D_{Hj}$ and fixation mark positions $F_{Hj}$ in the storage unit 120. Note that in this embodiment, the high-magnification images $D_{Hj}$ are moving images that have undergone inter-frame alignment.

(Image Display Processing)

Details of image display processing executed in step S550 will be described next with reference to the flowchart of FIG. 9.

<Step S910>

A representative image is generated from each of the moving images obtained by the wide viewing angle image obtaining unit 111 and the high-magnification image obtaining unit 112. In this embodiment, an overlap image for each moving image is generated, and this overlap image is set as a representative image. The representative image generation method is not limited to this. For example, a reference frame set at the time of inter-frame alignment of each moving image may be set as the representative image. As the reference frame setting method, an arbitrary known setting method is usable, and, for example, the frame of the first number can be set as the reference frame.

<Step S920>

When a plurality of high-magnification images $D_{Hj}$ are obtained, the display control unit 131 corrects the density difference between the high-magnification images. To correct the density difference, an arbitrary known luminance correction method is applicable. For example, in this embodiment, a histogram Hj of each high-magnification image $D_{Hj}$ is generated, and the luminance value of each high-magnification image $D_{Hj}$ is linearly converted such that the average and variance of the histogram Hj have values common to the high-magnification images $D_{Hj}$, thereby correcting the density difference.

<Step S930>

When displaying each high-magnification image $D_H$ as a moving image on the wide viewing angle image $D_L$, the display control unit 131 sets the reproduction speed of the high-magnification image $D_H$. The reproduction speed is adjusted by arranging a reproduction speed adjustment slider or a frame-by-frame advance button in an image display area and causing the operator to designate the reproduction speed via the instruction obtaining unit 140.

Note that in this embodiment, this processing is omitted because still images (overlap images) generated in step S910 are pasted together and displayed.

<Step S940>

The display control unit 131 controls display/non-display and the display magnification of each high-magnification image $D_{Hj}$. Display/non-display of an image is set by displaying a list associated with obtained images on the monitor 305, arranging a UI (in this embodiment, a check box) near the image names of the obtained image list, and causing the operator to designate ON/OFF of the UI via the instruction obtaining unit 140. A UI (check box) used to designate all images at once and a UI (check box) used to designate images at once on the obtaining magnification basis are also prepared to facilitate switching of display/non-display of a number of images.

In this step, not only display/non-display of images, but also an overlap order in case when an overlap region exists between adjacent high-magnification images $D_{Hj}$ or a case when image capture is performed at the same fixation mark position a plurality of times is set. As the method of setting the overlap order of moving images, an arbitrary setting method including manual setting is usable. In this embodiment, the image quality index or fixation disparity amount of each image is calculated, and an image having the largest evaluation value, which is obtained using the linear sum of the image quality indices or fixation disparity amounts as an evaluation function, is set as the uppermost layer and displayed. As the image quality index, an arbitrary known index is usable. In this embodiment, the average luminance value of an image histogram is used. As the fixation disparity amount, a value obtained by adding, throughout the frames, the absolute values of translation distances between adjacent frames is used. Note that an arbitrary index is usable as long as it can evaluate the fixation disparity. As for the display magnification, a high-magnification image designated by the operator via the instruction obtaining unit 140 is enlarged and displayed on the monitor 305.

Note that although the wide viewing angle image $D_L$ is a single wide viewing angle SLO image in the above-described example, the present invention is not limited to this. For example, a synthesis image obtained by aligning the wide viewing angle images $D_{Li}$ at different obtaining positions may be used as the wide viewing angle image $D_L$.

As described above, the ophthalmologic apparatus 10 according to this embodiment causes the operator to select a pattern from basic patterns associated with a plurality of high-magnification image obtaining parameters (image capture conditions), adjusts the parameter values in accordance with the lesion shape, and obtains high-magnification images based on the adjusted parameter values. More specifically, the ophthalmologic apparatus 10 selectively presents a plurality of basic patterns each representing the distribution of a plurality of positions to capture high-magnification images to the operator. Image capture conditions associated with capture of high-magnification images, which are associated in advance with a basic pattern selected from the plurality of basic patterns in accordance with selection of the operator, are adjusted based on an instruction of the operator. The image capture apparatus captures a plurality of high-magnification images in the image capture region in accordance with the adjusted image capture conditions. Hence, according to this embodiment, it is possible to easily set appropriate image capture conditions to obtain, in a given image capture region, a plurality of high-magnification images having a viewing angle smaller than that of the image capture region. This makes it possible to efficiently capture tissues, cells, or lesion candidates whose distribution changes depending on the eye to be examined in a range wider than a high-magnification image.

In this embodiment, an image capture condition is adjusted based on at least one of the position of the representative point of the selected basic pattern in the image capture region, a constraint condition designated by the operator, and the change amount of the image capture condition. It is, therefore, possible to easily set an appropriate image capture condition in accordance with the image capture target. For example, cells, tissues, and lesion shapes or densities have individual differences, and the region to be observed or measured specifically changes depending on the eye to be examined. According to the arrangement of this embodiment, after a cell, tissue, or lesion region of an observation target is specified for each eye to be examined, the obtaining parameters of the plurality of high-magnification images $D_{Hj}$ can automatically be set in accordance with the shape or density of the region.

Note that in this embodiment, a position in a wide viewing angle image at which a high-magnification image is to be captured, an image capture order, the number of images to be captured at the same position, the viewing angle and pixel size of a high-magnification image, the number of frames of image capture, the frame rate, and the in-focus position have been exemplified as the image capture conditions. However, the image capture conditions are not limited to those.

Second Embodiment

An ophthalmologic apparatus according to this embodiment is configured, when obtaining a plurality of high-magnification adaptive optics SLO images, to determine parameter values associated with obtaining of the plurality of high-magnification images based on image features extracted from an image having a viewing angle wider than that of the high-magnification images. More specifically, when obtaining a plurality of high-magnification images $D_{1j}$ in an annular pattern for a parafoveal capillary vessel region, the obtaining position, the viewing angle, the pixel size, the number of frames, the frame rate, and the repetitive obtaining count of each high-magnification image $D_{1j}$ are determined based on the image features. In addition, it is judged whether each obtained high-magnification image includes an exceptional frame such as a fixation disparity or nictation, and upon judging based on the judgment result that re-obtaining of the high-magnification image is necessary, the high-magnification image is obtained based on the same image obtaining parameter values.

(Overall Arrangement)

Figure 1B:
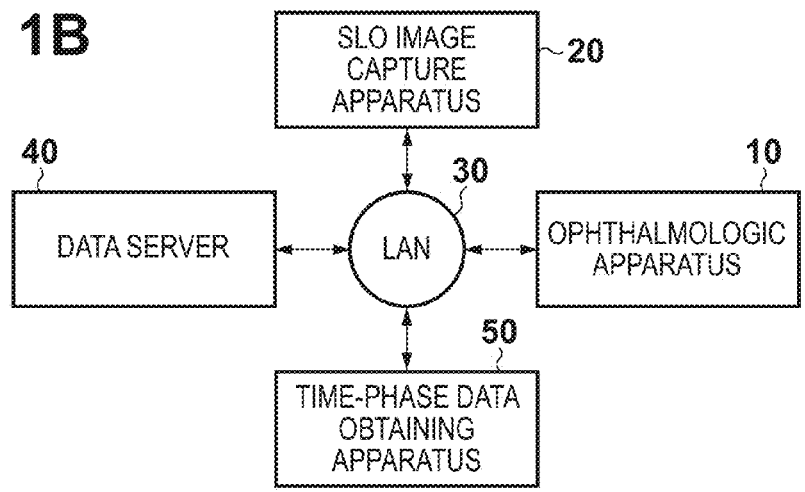

FIG. 1B shows the arrangement of apparatuses connected to an ophthalmologic apparatus 10 according to this embodiment. This embodiment is different from the first embodiment in that a time-phase data obtaining apparatus 50 is connected to the ophthalmologic apparatus 10 in addition to an SLO image capture apparatus 20 and a data server 40. The time-phase data obtaining apparatus 50 obtains biomedical signal data (called "time-phase data") that changes autonomously and periodically, and is formed from, for example, a pulse wave detector or an electrocardiograph. The time-phase data obtaining apparatus 50 obtains high-magnification images $D_{Hj}$, and simultaneously obtains time-phase data Sj in accordance with an operation of an operator (not shown). The obtained time-phase data Sj is transmitted to the ophthalmologic apparatus 10 and the data server 40. In this embodiment, high-magnification images are obtained in synchronism with a periodical timing represented by the time-phase data measured from a subject and displayed on a monitor 305. It is therefore possible to obtain or to reproduce a high-magnification image at an appropriate timing in accordance with a change in a living body.

The data server 40 holds the time-phase data Sj, image features of an eye, and normal values associated with the distribution of image features of an eye in addition to a wide viewing angle image $D_L$ and high-magnification images $D_H$ of an eye to be examined and obtaining condition data such as fixation mark positions $F_L$ and $F_H$ used at the time of obtaining. In this embodiment, blood vessels of retina, capillary vessels Q, and blood cells W are held as the image features of an eye. However, the image features are not limited to those. The data server 40 stores the time-phase data Sj output from the time-phase data obtaining apparatus 50 and the image features of the eye output from the ophthalmologic apparatus 10. In response to a request from the ophthalmologic apparatus 10, the data server 40 transmits the time-phase data Sj, the image features of the eye, and normal value data associated with the distribution of the image features of the eye to the ophthalmologic apparatus 10.

(Ophthalmologic Apparatus)

FIG. 10 illustrates the functional blocks of the ophthalmologic apparatus 10 according to this embodiment. The ophthalmologic apparatus 10 according to this embodiment includes a time-phase data obtaining unit 113 in a data obtaining unit 110, an image feature obtaining unit 134 in an image processing unit 130, a re-obtaining necessity determination unit 1325 in a determination unit 132, and an exceptional frame judgment unit 1331 in an alignment unit 133 in addition to the arrangement of the first embodiment. The time-phase data obtaining unit 113 is a functional block that obtains the time-phase data of a subject. The image feature obtaining unit 134 is a functional block that analyzes the wide viewing angle image and obtains information of image features thereof. The re-obtaining necessity determination unit 1325 is a functional block that judges whether to obtain a high-magnification image again. The exceptional frame judgment unit 1331 is a functional block that detects a frame unsuitable for optometry such as a frame including a large misalignment caused by a fixation error as an "exceptional frame". When an "exceptional frame" is detected, the high-magnification image is re-obtained.

(Processing Procedure)

The image processing procedure according to this embodiment is the same as that in FIG. 5, and the processes of steps S510, S560, S570, and S580 are the same as those in the first embodiment. Step S540 is omitted. In this embodiment, the processes of steps S520, S530, and S550 will be described.

<Step S520>

An image obtaining pattern presentation unit 1311 obtains at least one type of image obtaining pattern when obtaining a plurality of high-magnification images from a storage unit 120 and displays it on the monitor 305. In this embodiment, the image obtaining pattern presentation unit 1311 presents linear, cruciform, radial, rectangular, disc-shaped, annular, multiple magnification, multiple arrangement, and composite basic patterns.

An instruction obtaining unit 140 externally obtains an instruction about which image obtaining pattern should be selected. In this embodiment, an example will be explained in which the observation target is an annular parafoveal capillary vessel region as shown in FIG. 7C. In this case, it is necessary to determine the inner boundary of the annular region based on an avascular region. Hence, the operator selects the multiple magnification image obtaining pattern. In the multiple magnification image obtaining pattern, images $D_{1j}$ form an annular pattern, and images $D_{2k}$ form a rectangular pattern.

Note that in this embodiment, the image obtaining pattern selection processing is not essential, and the processing of this step may be omitted by setting the high-magnification image obtaining target region to an annular region and the intermediate-magnification image obtaining target region to a rectangular region from the beginning.

<Step S530>

The determination unit 132 requests a high-magnification image obtaining unit 112 to obtain the intermediate-magnification images $D_{2k}$, and the high-magnification image obtaining unit 112 obtains the intermediate-magnification images $D_{2k}$. Next, the image feature obtaining unit 134 obtains image features on the wide viewing angle image $D_L$ and the intermediate-magnification images $D_{2k}$. The obtaining parameters of the plurality of high-magnification images are determined based on the image features, and the high-magnification images $D_{1j}$ are obtained. Inter-frame alignment and exceptional frame judgment are performed for the obtained high-magnification image $D_{1j}$. Upon judging based on the exceptional frame judgment result that re-capture is necessary, the same high-magnification image $D_{1j}$ is captured again. The intermediate-magnification images $D_{2k}$ and the high-magnification images $D_{1j}$ are aligned on the wide viewing angle image $D_L$. The processing (high-magnification image obtaining processing) of this step will be described later in detail with reference to the flowchart of FIG. 11.

<Step S550>

A display control unit 131 superimposes the high-magnification images DH on the wide viewing angle image DL and displays them, as shown in FIG. 7E, based on the alignment parameter values obtained in step S1270 (to be described later). In this embodiment, capillary vessel images as shown in FIG. 7F are pasted and displayed at positions adjacent to the superimposed images as images that allow the user to more specifically observe the distribution of the parafoveal capillary vessels. As described above, in this embodiment, display control is performed so as to superimpose the plurality of captured high-magnification images on the image representing the entire image capture region and display them on the monitor 305. It is, therefore, possible to observe a precise image only in a necessary portion of the wide viewing angle image. The processing (image display processing) of this step will be described later in detail with reference to the flowchart of FIG. 9.

(High-Magnification Image Obtaining Processing)

Details of processing executed in step S530 will be described next with reference to the flowchart of FIG. 11.

<Step S1210>

The determination unit 132 obtains the intermediate-magnification images $D_{2k}$ based on the image obtaining pattern selected in step S520 for the images $D_{2k}$.

Figure 12A:
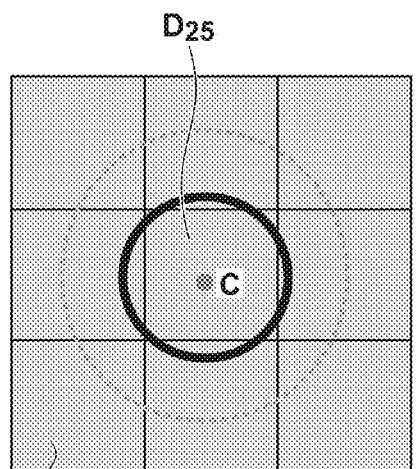
FIGS. 12A to 12C are views for explaining an image obtaining pattern and exceptional frames included in a high-magnification moving image.

In this embodiment, a rectangular image obtaining pattern as indicated by the images $D_{2k}$ of FIG. 12A is set. A fixation mark is presented such that a central point C of the image obtaining pattern is located near the fovea centralis. In addition, 600 [µm]×600 [µm], 2 [µm/pixel]×2 [µm/pixel], 256, and 64 [frames/sec] are set as the values of the viewing angle, the pixel size, the number of frames, and the frame rate, respectively. The overlap region between adjacent intermediate-magnification images is assumed to be 10% of the intermediate-magnification image area. In this embodiment, the obtaining order of the high-magnification images is set such that an intermediate-magnification image $D_{25}$ at the center of the image obtaining pattern is set as the first obtaining position, and the obtaining position is moved to the next image on the right side and then moved counterclockwise through the adjacent images. The alignment unit 133 performs inter-frame alignment of the obtained intermediate-magnification images $D_{2k}$, and alignment (image paste) of the intermediate-magnification images $D_{2k}$ on the wide viewing angle image DL. Note that the coordinate transformation method and the degree of similarity evaluation function used for the alignment are the same as in the first embodiment, and a detailed description thereof will be omitted.

<Step S1220>

The image feature obtaining unit 134 detects capillary vessels from the wide viewing angle image $D_L$ or the intermediate-magnification images $D_{2k}$ obtained in step S1210, and detects the boundary of an avascular region from the detected capillary vessel region. To set a region near the avascular region as the high-magnification image obtaining target region, an annular (doughnut) region equidistant from the boundary position of the avascular region is detected.

In this embodiment, first, capillary vessels are specified from the intermediate-magnification images $D_{2k}$ as a blood cell component moving range in accordance with the following procedures.

(a) Difference processing is performed between adjacent frames of each intermediate-magnification image D2*k* that has undergone inter-frame alignment. That is, a difference moving image is generated.

(b) The luminance statistic (for example, variance) concerning the frame direction is calculated at each x-y position of the difference moving image generated in (a).

(c) A region in which the luminance variance at each x-y position of the difference moving image is equal to or larger than a threshold Tv is specified as a region where blood cells move, that is, a capillary vessel region.

Note that capillary vessel detection processing is not limited to this method, and an arbitrary known method is usable. For example, blood vessels may be detected by applying a filter that enhances a linear structure to a specific frame of the wide viewing angle image $D_L$ or the intermediate-magnification image $D_{2k}$.

Next, the image feature obtaining unit 134 detects the boundary of an avascular region from the obtained capillary vessel region. A region (to be referred to as an "avascular region") including no capillary vessels exists near the fovea centralis of a retina, as indicated by the interior of an inner broken line region in FIG. 7C. The boundary shapes of avascular regions have large individual differences, and an initial lesion of a blood vessel of retina readily occurs around the avascular region boundary. Hence, the avascular region boundary is important as an observation and analysis target.

Figure 12B:
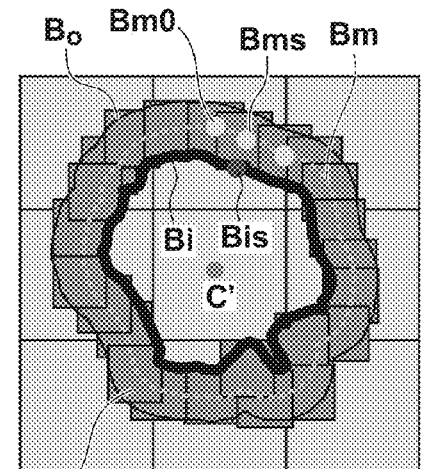

In this embodiment, a deformable model (solid line portion in FIG. 12A) having a radius Tr smaller than that of a circle (broken line portion in FIG. 12A) that connects the image centers of the high-magnification images $D_{1j}$ in the image obtaining pattern is arranged on the pasted image of the intermediate-magnification images $D_{2k}$ aligned on the wide viewing angle image in step S1210. In this embodiment, the model is arranged such that its center coincides with the center C of the intermediate-magnification image $D_{25}$ in FIG. 12A. The position (Bi in FIG. 12B) of the deformable model, which has completed deformation according to the image features on the pasted image of the intermediate-magnification images $D_{2k}$, is defined as the avascular region boundary, and a center-of-gravity position C' of the avascular region boundary is determined. In addition, positions (Bo and Bm in FIG. 12B) apart from the avascular region boundary outward by distances of predetermined thresholds To and To/2 are determined using distance images (images having distance values from the boundary as pixel values) obtained by performing Euclidean distance transformation for the avascular region boundary. An arbitrary value can be set as the threshold To. In general, the value is often set to about 150 [μm] for a person without any disability, and therefore, this value is used in this embodiment as well. An annular (doughnut) high-magnification image capture target region is determined using the specified inner boundary Bi and outer boundary Bo. The broken line portion Bm indicates the candidates of the obtaining positions (image centers) of the high-magnification images $D_{1j}$.

Note that in this embodiment, the distance (thickness of the annular region) from the avascular region boundary is fixed by the threshold To. However, the present invention is not limited to this. For example, in a disease such as diabetic retinopathy having lesions in parafoveal capillary vessels of retina, capillary vessel occlusion occurs along with the disease progression, and the avascular region becomes large. When the avascular region is large, vascular lesions may have occurred in a wider range around the avascular region. Hence, a value obtained by multiplying the threshold To by a value proportional to the area of the avascular region may be set as the distance from the avascular region boundary. Note that in this case, the viewing angle is set as a variable parameter and determined to have a value much larger than the distance from the avascular region boundary, that is, the thickness of the annular region in step S1230.

<Step S1230>

A magnification determination unit 1321 determines the number of magnifications, the viewing angle, and the pixel size of the high-magnification images $D1j$. A position determination unit 1322 determines the obtaining position and the in-focus position of each high-magnification image $D1j$. In this embodiment, the number of magnifications, the viewing angle, the pixel size, and the in-focus position are set as fixed parameters (respectively set to 2, 200 [μm]×200 [μm], 1 [μm/pixel]×1 [μm/pixel], and capillary vessel), and the obtaining position of each high-magnification image D is set as a variable parameter. These parameters are determined in the following way.

First, points (Bms in FIG. 12B) obtained by sampling the boundary Bm determined in step S1220 at an equal interval Td are defined as the candidates of the obtaining positions of the high-magnification images $D_{1j}$. The obtaining positions of the high-magnification images $D_{1j}$ are sequentially determined from a specific candidate point Bm0.

In this embodiment, interval Td=viewing angle of high-magnification image $D_{1j}$(100−standard value of ratio of overlap region between high-magnification images $D_{1j}$)/100 (1)

A candidate point immediately above the center-of-gravity position of the avascular region is set to Bm0. Specific obtaining positions of the high-magnification images $D_{1j}$ are determined so as to meet both conditions:

(a) the total number of pixels of the high-magnification images D1j located outside the annular region is minimized under a condition that no blanks are formed in the annular region concerning the radial direction of the annular region determined in step S1220 (the direction of a line that connects the center-of-gravity position C' of the avascular region and the obtaining position candidate point Bms); and (b) matching with the ratio of the overlap region between the high-magnification images to be described below is obtained concerning the tangential direction of the boundary position Bm.

In this case, a value obtained by multiplying a standard set value (for example, 20% in this embodiment) by a value inversely proportional to a circularity Cr of the avascular region boundary specified in step S1220 is set as the ratio [%] of the overlap region between the high-magnification images $D_{1j}$. The circularity Cr is given by $Cr=4\pi S/(L*L)$ (2)

where S is the area of the avascular region boundary, and L is the boundary length. Hence, the lower the circularity is, that is, the larger the unevenness is, the larger the value set as the ratio of the overlap region between the high-magnification images $D_{1j}$ is.

The method of determining the overlap region between the high-magnification images is not limited to this, and an arbitrary known method is usable. For example, the absolute values of curvatures are calculated within the range of a predetermined distance in the direction of high-magnification images adjacent along the avascular region boundary from an intersection Bis between the avascular region and the line that connects the center C' of gravity of the avascular region boundary and the obtaining position candidate point Bms, and an average value Ch of the obtained absolute values of the curvatures is calculated. The standard set value associated with the ratio of the overlap region between the high-magnification images is multiplied by a value proportional to the average curvature value Ch and thus weighted. When the average curvature value Ch is zero, the standard set value is directly used without being weighted. When this setting method is used, the ratio of the overlap region between the high-magnification images can be set large in the neighborhood of a position where the absolute value of the curvature of the avascular region boundary is large.

<Step S1240>

A time determination unit 1323 determines the number of frames, the frame rate, and the repetitive obtaining count of the high-magnification images D1j. In the example of this embodiment, the number of frames, the frame rate, and the repetitive obtaining count at the same position are set to 256, 64 [frames/sec], and 2, respectively. However, the present invention is not limited to this, and an arbitrary setting method is usable. For example, thinning processing is performed for a capillary vessel region in each high-magnification image $D_{1j}$ determined by the processes of steps S1220 and S1230, and the vascular diameter in a direction perpendicular to the central axis of the obtained blood vessel is calculated. Only when a region where the vascular diameter exhibits an abnormal value exist, the number of frames and the repetitive obtaining count of the high-magnification image $D_{1j}$ may be increased by thresholds Tf and Tc, respectively.

<Step S1250>

An order determination unit 1324 determines the obtaining order of the high-magnification images $D_{Hj}$. As in step S850 of the first embodiment, repetitive processing is performed by setting, out of (i) to (iii) to be described below, (i) as the innermost loop (highest priority), (ii) as the second inner loop, and (iii) the outermost loop (lowest priority). More specifically, the following procedures are executed by setting the obtaining start position on an ear side and the obtaining magnification to the lowest magnification:

(i) obtain images of the same obtaining magnification and same image obtaining position as many as the repetitive obtaining count;

(ii) obtain images of the same obtaining magnification from an adjacent image obtaining position (in this embodiment, counterclockwise) as in i); and (iii) when (ii) has ended, increase the value of the obtaining magnification, execute the operation (ii) again, and repeat the same operation as many times as the number of magnifications.

Note that the high-magnification image order determination method is not limited to the above-described procedure, and an arbitrary order setting method is usable.

<Step S1260>

The high-magnification image obtaining unit 112 obtains high-magnification images and time-phase data in accordance with the high-magnification image obtaining parameters determined in steps S1210 to S1250. The time-phase data obtaining unit 113 requests the time-phase data obtaining apparatus 50 to obtain the time-phase data Sj associated with a biomedical signal. In this embodiment, a pulse wave detector is used as the time-phase data obtaining apparatus, and the time-phase data Sj is obtained from a lobulus auriculae (earlobe) of a subject. The time-phase data Sj is expressed as a periodical point sequence having obtaining times along one axis and pulse wave signal values measured by the pulse wave detector along the other axis. In response to the obtaining request, the time-phase data obtaining apparatus 50 obtains the corresponding time-phase data Sj and transmits it. Hence, the time-phase data obtaining unit 113 receives the time-phase data Sj from the time-phase data obtaining apparatus 50 via the LAN 30. The time-phase data obtaining unit 113 stores the received time-phase data Sj in the storage unit 120.

The data obtaining unit 110 requests the SLO image capture apparatus 20 to obtain the wide viewing angle image $D_L$, the plurality of high-magnification images $D_{Hj}$ captured at different fixation mark positions Fj, and the data of the fixation mark position Fj. Two cases can be considered here: a case when the data obtaining unit 110 starts obtaining the high-magnification images $D_{Hj}$ in accordance with a certain phase of the time-phase data Sj obtained by the time-phase data obtaining apparatus 50; and a case when obtaining of the time-phase data Sj and that of the high-magnification images $D_{Hj}$ are simultaneously started immediately after the obtaining request of the high-magnification images $D_{Hj}$. In this embodiment, immediately after the obtaining request of the high-magnification images $D_{Hj}$, obtaining of the time-phase data Sj and that of the high-magnification images $D_{Hj}$ are started.

<Step S1270>

The alignment unit 133 performs inter-frame alignment associated with the obtained high-magnification images $D_{1j}$, aligns the high-magnification images $D_{1j}$ on wide viewing angle image $D_L$, and displays them on the monitor 305. Note that in this embodiment, exceptional frame judgment of judging whether a frame corresponds to an exceptional frame to be described below is performed at the time of inter-frame alignment of each high-magnification image $D_{1j}$. As the inter-frame alignment method for each moving image or the alignment (image paste) method for images of different magnifications, an arbitrary known alignment method is usable. In this embodiment, both alignment processes are performed using affine transformation and a correlation function.

Figure 12C:
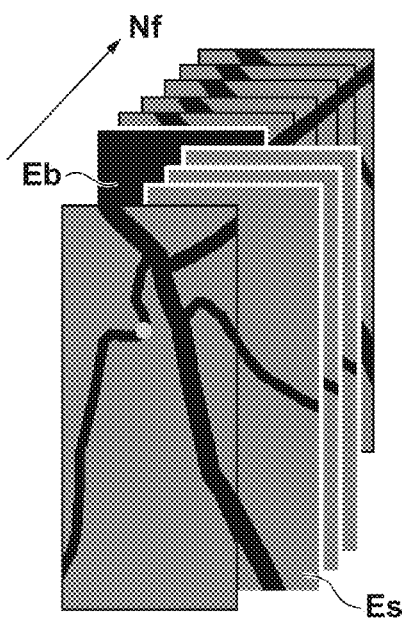

As shown in FIG. 12C, an exceptional frame means a frame Es greatly misaligned due to poor fixation, a low-luminance frame Eb generated by nictation, or a low-quality frame (not shown) generated by an aberration correction error in the high-magnification image $D_H$. An exceptional frame can be judged based on whether each of the degree of luminance abnormality, the magnitude of distortion, the level of noise with respect to a signal, and a displacement amount with respect to a reference frame is a predetermined value or more. More specifically, (a) when out of the alignment parameter values between frames, translation is equal to or larger than a threshold, (b) when the average luminance value of a frame is smaller than a threshold, and (c) when the S/N ratio of a frame is smaller than a threshold, the frame is judged as an exceptional frame. Upon judging by the exceptional frame judgment that the maximum value of the exceptional frame generation interval in a high-magnification image $D_{1j}$ is equal to or less than a threshold Te, or the total number of exceptional frames is equal to or greater than a threshold Ts, the re-obtaining necessity determination unit 1325 judges that re-obtaining of the high-magnification image $D_{1j}$ is necessary. Upon judging that re-obtaining of the high-magnification image $D_{1j}$ is necessary, the re-obtaining necessity determination unit 1325 requests the high-magnification image obtaining unit 112 to re-obtain the high-magnification image $D_{1j}$, and the high-magnification image obtaining unit 112 re-obtains the high-magnification image $D_{1j}$ in response to the request.

Note that the inter-frame alignment, exceptional frame judgment, re-obtaining necessity judgment, and re-obtaining need not always be executed after all high-magnification images are obtained. For example, exceptional frame judgment and re-obtaining necessity judgment may be executed immediately after a high-magnification image is obtained, and the high-magnification image may be re-obtained as soon as it is judged that it needs to be re-obtained. Alternatively, at the time of inter-frame alignment of the intermediate-magnification images $D_{2k}$ in step S1210, exceptional frame judgment and re-obtaining necessity judgment may be executed, and the intermediate-magnification images $D_{2k}$ may be re-obtained as soon as it is judged that they need to be re-obtained. Otherwise, the exceptional frame judgment need not always be executed only at the time of inter-frame alignment of the SLO moving image. For example, an anterior camera may be connected to the ophthalmologic apparatus 10, and judgment may be done using image processing of the anterior camera, for example, low-luminance frame detection, pupil position detection, or the like.

(Image Display Processing)

Details of processing executed in step S550 will be described next with reference to the flowchart of FIG. 9. Note that processes except steps S910 and S930 are the same as those in the first embodiment, and processes of steps S910 and S930 will be described in this embodiment.

<Step S910>

The display control unit 131 performs processing of generating superimposed images of the high-magnification images $D_H$ on the wide viewing angle image $D_L$ as shown in FIG. 7E based on the alignment parameter values obtained in step S1270. In this embodiment, since the high-magnification images $D_H$ are pasted and displayed as not still images, but moving images, as will be explained concerning step S930, no representative image is generated. However, an image that has undergone inter-frame alignment may include, at an image end, a region that has pixel values zero and hinders the display. Hence, at an image end upon displaying the pasted image, only pixels having pixel values greater than zero are displayed throughout all frames other than exceptional frames.

In this embodiment, capillary vessel images as shown in FIG. 7F are also pasted and displayed adjacently to the pasted moving image as images that allow the user to more specifically observe the distribution of parafoveal capillary vessels. As for the capillary vessel images, the capillary vessel region specifying processing executed for the intermediate-magnification images $D_{2k}$ in step S1220 is performed for not only the intermediate-magnification images $D_{2k}$ but also the high-magnification images $D_{1j}$, thereby generating binary images, which are pasted and displayed based on the alignment parameters obtained in step S1270. Even in the capillary vessel images, only pixels having pixel values greater than zero are displayed throughout all frames other than exceptional frames, as in pasting the moving images.

<Step S930>

When displaying the plurality of intermediate-magnification images $D_{2k}$ or high-magnification images $D_{1j}$ on the wide viewing angle image $D_L$, the reproduction timings of the intermediate-magnification images $D_{2k}$ and the high-magnification images $D_{1j}$ are synchronized based on time-phase data (periodical data based on a biomedical signal such as a pulse wave). More specifically, the display control unit 131 obtains time-phase data Sj and Sk corresponding to the moving images (that is, the high-magnification images $D_{1j}$ and the intermediate-magnification images $D_{2k}$) from the time-phase data obtaining unit 113, detects the extreme value of each time-phase data, and calculates the pulsating period. Next, the display control unit 131 obtains an exceptional frame number sequence in each of the high-magnification images $D_{1j}$ and the intermediate-magnification images $D_{2k}$, and selects a continuous frame sequence including no exceptional frame as a display target. When the pulsating period in the selected frames changes between the moving images (high-magnification images $D_{1j}$ or intermediate-magnification images $D_{2k}$), adjustment processing (to be referred to as "frame interpolation processing") of the display frame interval between the moving images is performed. In addition, a pasted moving image is displayed by reproducing frames corresponding to an integer multiple of the pulsating period while adjusting the reproduction start time of each moving image such that the reproduction timings of frames corresponding to the extreme values of the time-phase data corresponding to the respective moving images match.

Note that the display method of the present invention is not limited to this. If no time-phase data is obtained, this step may be omitted, and the moving images may be pasted and displayed without adjusting the reproduction times.

As described above, the ophthalmologic apparatus 10 according to this embodiment determines parameter values associated with obtaining a plurality of high-magnification images based on image features extracted from an image having a viewing angle wider than that of the high-magnification images when obtaining a plurality of high-magnification adaptive optics SLO images. This makes it possible to efficiently capture tissues, cells, or lesion candidates whose distribution changes depending on the eye to be examined in a range wider than a high-magnification image.

In this embodiment, based on image features associated with a blood vessel or a region where blood cells move, at least one blood vessel image is displayed on the monitor 305 from captured high-magnification images. This makes it possible to appropriately extract only a portion that needs particularly careful observation from a wide viewing angle image and automatically perform precise image capture/display.

Third Embodiment

An ophthalmologic apparatus according to this embodiment is configured to determine parameter values associated with obtaining a plurality of high-magnification images based on image features extracted from an OCT tomogram having a viewing angle wider than that of high-magnification images when obtaining a plurality of high-magnification adaptive optics OCT tomograms. More specifically, the operator selects a basic pattern for obtaining a plurality of high-magnification images in a disc-shaped pattern for a visual cell layer near the fovea centralis where the extraretinal layer deforms due to serous retinal detachment RD and sets the initial values of image obtaining parameters. Next, the obtaining parameters (obtaining position, viewing angle, pixel size, and coherence gate) of the plurality of high-magnification images are changed based on the image features of a layer shape obtained from a wide viewing angle OCT tomogram, and images are captured. This case will be explained.

(Overall Arrangement)

Figure 1C:
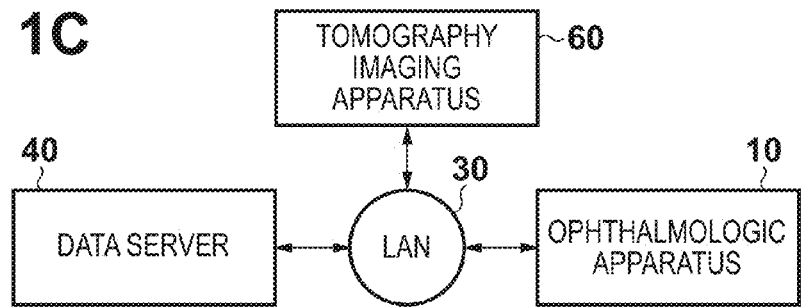

FIG. 1C shows the arrangement of apparatuses connected to an ophthalmologic apparatus 10 according to this embodiment. This embodiment is different from the first embodiment in that the ophthalmologic apparatus 10 is connected not to the SLO image capture apparatus 20, but to a tomography imaging apparatus 60 including an adaptive optics system. The tomography imaging apparatus 60 captures a tomogram of an eye. The tomography imaging apparatus 60 is formed as, for example, SD-OCT (Spectral Domain Optical Coherence Tomography). The tomography imaging apparatus 60 three-dimensionally captures the tomograms of an eye to be examined in accordance with the operation of an operator (not shown). The captured tomograms are transmitted to the ophthalmologic apparatus 10.

(Ophthalmologic Apparatus)

FIG. 13 illustrates the functional blocks of the ophthalmologic apparatus 10 according to this embodiment. This arrangement is different from that of the first embodiment in that an image processing unit 130 includes an image feature obtaining unit 134 that obtains the features of a wide viewing angle image. A data server 40 holds image features of an eye and normal value data associated with the distribution of image features of an eye. A case when normal value data concerning a retinal layer boundary and a shape and thickness thereof are held as the data will be described here.

(Tomography Imaging Apparatus)

Figure 14:
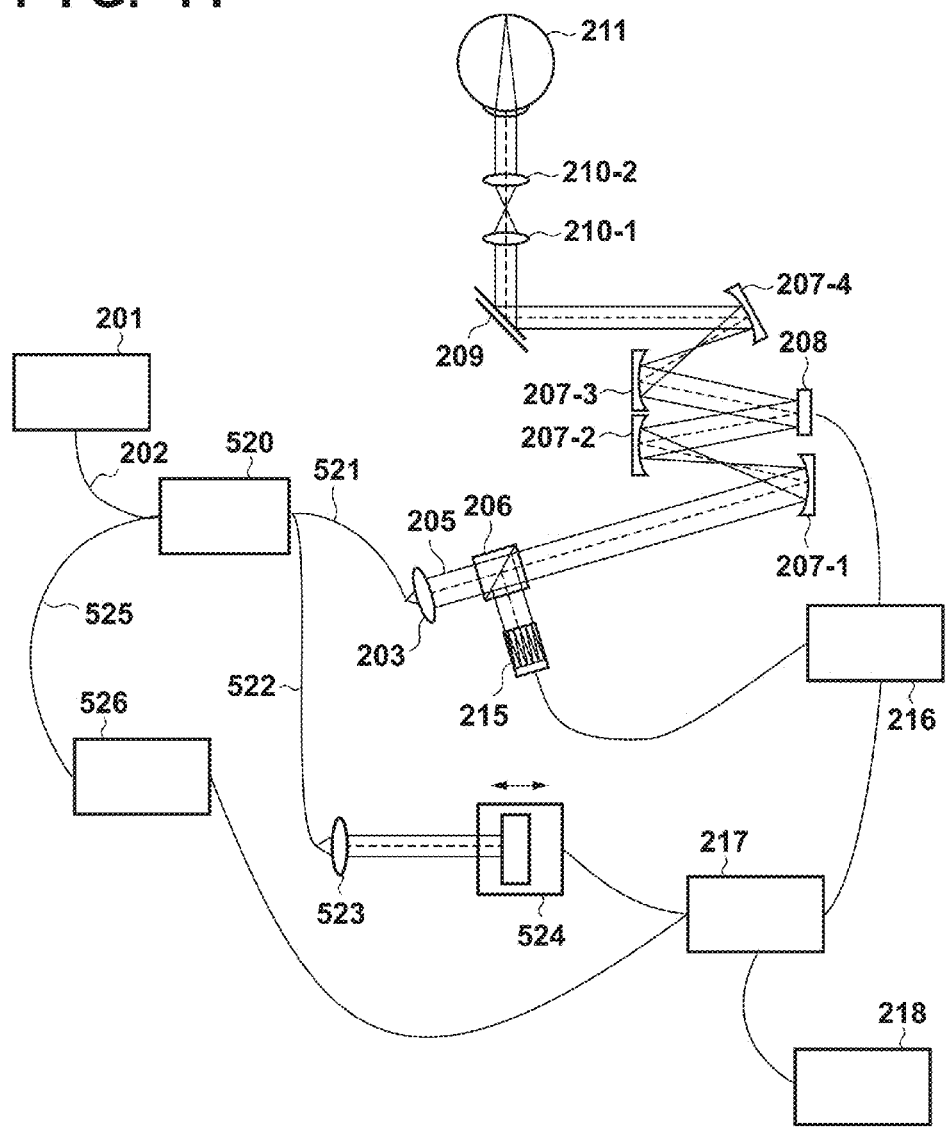
FIG. 14 is a view for explaining the overall arrangement of a tomography imaging apparatus 60.

The arrangement of the tomography imaging apparatus 60 including an adaptive optics system will be described next with reference to FIG. 14. Referring to FIG. 14, reference numeral 201 denotes a light source. In this embodiment, an SLD having a wavelength of 840 nm is used. The light source 201 need only be of a low coherence type, and an SLD having a wavelength of 30 nm or more is suitably used. An ultrashort light pulse laser, such as a titanium sapphire laser, is also usable as the light source. Light emitted by the light source 201 passes through a single-mode optical fiber 202 and is guided to a fiber coupler 520. The fiber coupler 520 branches the optical path into a measurement light path 521 and a reference light path 522. The fiber coupler 520 uses a fiber coupler having a branching ratio of 10:90 and is configured to make light corresponding to 10% of the input light amount reach the measurement light path 521. The light that has passed through the measurement light path 521 exits from a collimator 203 as parallel measurement light.

The arrangement from the collimator 203 is the same as in the SLO image capture apparatus 20 described in the first embodiment. More specifically, the light passes through an adaptive optics system and a scanning optical system and irradiates an eyeball 211. Reflected/scattered light from the eyeball 211 travels through the same path again, and is guided by the optical fiber 521 up to the fiber coupler 520. On the other hand, light that has passed through the reference light path 522 exits from a collimator 523 and is reflected by an optical path length changing unit 524 and returned to the fiber coupler 520 again. The measurement light and the reference light, which have reached the fiber coupler 520, are combined and guided to a spectroscope 526 via an optical fiber 525. A control unit 217 constructs a tomogram of an eye based on interference light information spectrally obtained by the spectroscope 526. The control unit 217 can control the optical path length changing unit 524 and obtain an image at a desired depth position.

Note that in the arrangement shown in FIG. 14, when the swing angle of the scanning optical system is increased, and an adaptive optics control unit 216 instructs not to correct aberrations, the tomography imaging apparatus 60 can operate as a normal tomography imaging apparatus and capture a wide viewing angle tomogram (wide viewing angle image DL). In this embodiment, the tomography imaging apparatus 60, including the adaptive optics system, is formed as an SD-OCT. However, forming an SD-OCT is not essential. For example, the tomography imaging apparatus may be formed as time-domain OCT or SS-OCT (Swept Source Optical Coherence Tomography). In SS-OCT, a light source that generates light beams of different wavelengths at different timings is used, and a spectral element configured to obtain spectral information is unnecessary. Additionally, an SS-OCT can obtain a deeply invasive image including not only a retina, but also a chorioidea.

(Processing Procedure)

FIG. 5 illustrates the image processing procedure of the ophthalmologic apparatus 10 according to this embodiment. The processing contents other than steps S510, S520, S530, S540, and S550 are the same as those of the first embodiment described with reference to FIG. 5. In this embodiment, the processes of steps S510, S520, S530, S540, and S550 will be described.

<Step S510>

A wide viewing angle image obtaining unit 111 requests the tomography imaging apparatus 60 to obtain a wide viewing angle image $D_L$ and a fixation mark position $F_L$. In this embodiment, an example will be explained in which the wide viewing angle image $D_L$ is obtained by setting the fixation mark position $F_L$ in the fovea centralis of a macular portion. Note that the image capture position setting method is not limited to this, and the image capture position may be set at another arbitrary position.

In response to the obtaining request from the wide viewing angle image obtaining unit 111, the tomography imaging apparatus 60 obtains the wide viewing angle image $D_L$ and the fixation mark position $F_L$ and transmits them to the wide viewing angle image obtaining unit 111. The wide viewing angle image obtaining unit 111 receives the wide viewing angle image $D_L$ and the fixation mark position $F_L$ from the tomography imaging apparatus 60 via a LAN 30. The wide viewing angle image obtaining unit 111 stores the received wide viewing angle image $D_L$ and fixation mark position $F_L$ in a storage unit 120.

<Step S520>

An image obtaining pattern presentation unit 1311 obtains at least one type of basic setting pattern (image obtaining pattern) associated with parameters when obtaining a plurality of high-magnification images from the storage unit 120 and displays it on a monitor 305. An arbitrary pattern can be set as the image obtaining pattern. In this embodiment, basic patterns as shown in FIGS. 15A to 15F are presented. More specifically, FIG. 15A shows a linear pattern, FIG. 15B shows a cruciform pattern, FIG. 15C shows a radial pattern, FIG. 15D shows a rectangular pattern, FIG. 15E shows a disc-shaped pattern, and FIG. 15F shows an annular pattern.

An instruction obtaining unit 140 externally obtains an instruction about which image obtaining pattern should to be selected. In this embodiment, a case when the observation target is a region where the extraretinal layer deforms due to the serous retinal detachment RD, and lesions occur in visual cells, as shown in FIG. 15I, will be described. Hence, the disc-shaped image obtaining pattern as shown in FIG. 15E is selected.

Note that, as in the first embodiment, multiple magnification, multiple arrangement, and composite image obtaining patterns may be presented even for a three-dimensional tomogram. For example, when a multiple magnification image obtaining pattern is selected, and the number of magnifications is three, an obtaining pattern of an intermediate-magnification image $D_{3m}$ as shown in FIG. 15H, an obtaining pattern of intermediate-magnification images $D_{2k}$ as shown in FIG. 15G, and an obtaining pattern of high-magnification images $D_{1j}$ as shown in FIG. 15E can be selected. For a multiple arrangement image obtaining pattern, a plurality of image obtaining patterns may be arranged in the depth direction (z-axis direction in FIGS. 15A to 15H) and presented.

<Step S530>

A determination unit 132 determines the obtaining parameters of a plurality of high-magnification images by setting the obtaining parameters of a plurality of images included in the image obtaining pattern selected in step S520 as initial values and adjusting the image obtaining parameters based on image features obtained by an image feature obtaining unit 134. The processing (high-magnification image obtaining processing) of this step will be described later in detail with reference to the flowchart of FIG. 16.

<Step S540>

An alignment unit 133 aligns the wide viewing angle image $D_L$ and high-magnification images $D_{Hj}$, and determines the positions of the high-magnification images $D_{Hj}$ on the wide viewing angle image $D_L$. First, the alignment unit 133 obtains a fixation mark position $F_{Hj}$ used when capturing the high-magnification images $D_{Hj}$ from the storage unit 120, and sets it as the initial point for an alignment parameter search in alignment between the wide viewing angle image DL and the high-magnification images $D_{Hj}$. If an overlap region exists between the high-magnification images $D_{Hj}$, first, the degree of similarity between the images is calculated concerning the overlap region, and the positions of the high-magnification images $D_{Hj}$ are aligned with a position where the degree of similarity between the images is maximum. Next, if high-magnification images having different resolutions are obtained in step S530, alignment is performed sequentially from an image of a lower magnification, as in the first embodiment. In this embodiment, since the high-magnification images have only one type of resolution, only alignment between the wide viewing angle image $D_L$ and the high-magnification image $D_H$ is performed.

Note that, as the degree of similarity between images or the coordinate transformation method, an arbitrary known method is usable. In this embodiment, alignment is performed using three-dimensional correlation coefficients as the degree of similarity between images and three-dimensional affine transformation as the coordinate transformation method.

<Step S550>

A display control unit 131 displays the high-magnification images $D_{Hj}$ on the wide viewing angle image $D_L$ based on the alignment parameter values obtained in step S540. In this embodiment, since both the wide viewing angle image $D_L$ and the high-magnification images $D_{Hj}$ are three-dimensional tomograms, the following two types of display are performed:

(i) projected images of the wide viewing angle image $D_L$ and the high-magnification images $D_{Hj}$ are generated concerning the z-axis direction, and the projected images of the high-magnification images $D_H$ are superimposed on the projected image of the wide viewing angle image $D_L$; and (ii) a wide viewing angle three-dimensional tomogram $D_L"$ is generated, which is expressed by the pixel values of the wide viewing angle three-dimensional tomogram $D_L$ at positions where only the wide viewing angle three-dimensional tomogram $D_L$ is obtained and by the pixel values of the high-magnification three-dimensional tomogram $D_{Hj}$ at positions where both the wide viewing angle three-dimensional tomogram $D_L$ and the high-magnification three-dimensional tomogram $D_{Hj}$ are obtained. A specific scanning position on the wide viewing angle three-dimensional tomogram $D_L"$ is displayed by an arrow on the superimposed image of (i). A two-dimensional tomogram of the wide viewing angle three-dimensional tomogram $D_L"$ is cut out at the position of the arrow and displayed beside the superimposed image as in (i). In this display, not only the two-dimensional tomogram of the wide viewing angle three-dimensional tomogram $D_L$, but also the two-dimensional tomogram of the high-magnification three-dimensional tomogram $D_{Hj}$ is superimposed and displayed. In display of (ii), the operator can move the arrow indicating the display position of the wide viewing angle tomogram $D_L"$ (in the vertical or horizontal direction) via the instruction obtaining unit 140. The display slices of the wide viewing angle image $D_L$ and the high-magnification images $D_{Hj}$, which are cut out and displayed, also change in synchronism with the operation.

When a plurality of high-magnification images $D_{Hj}$ of different obtaining positions are obtained, as in this embodiment, adjustment is performed to cause the high-magnification images $D_{Hj}$ to have a similar luminance characteristic using the same method as in the first embodiment. When the image capture positions of the high-magnification images $D_{Hj}$ are close to each other, and an overlap region exists (including a case when the image capture positions are the same), the display method of the overlap region is set to one of the following methods. That is, the image quality index value of each image is calculated, and an image having the largest evaluation value is displayed. Alternatively, the luminance of each high-magnification image $D_{Hj}$ is weighted by transparency based on the above-described image quality index value, and blending is performed. As the image quality index value, an arbitrary known index is usable. In this embodiment, the average luminance value of an image histogram is used.

Note that the method of generating the projected images is not limited to average value projection, and an arbitrary projecting method may be used. The high-magnification images $D_{Hj}$ are not limited to still images, and moving images may be used.

(High-Magnification Image Obtaining Processing)

Figure 16:
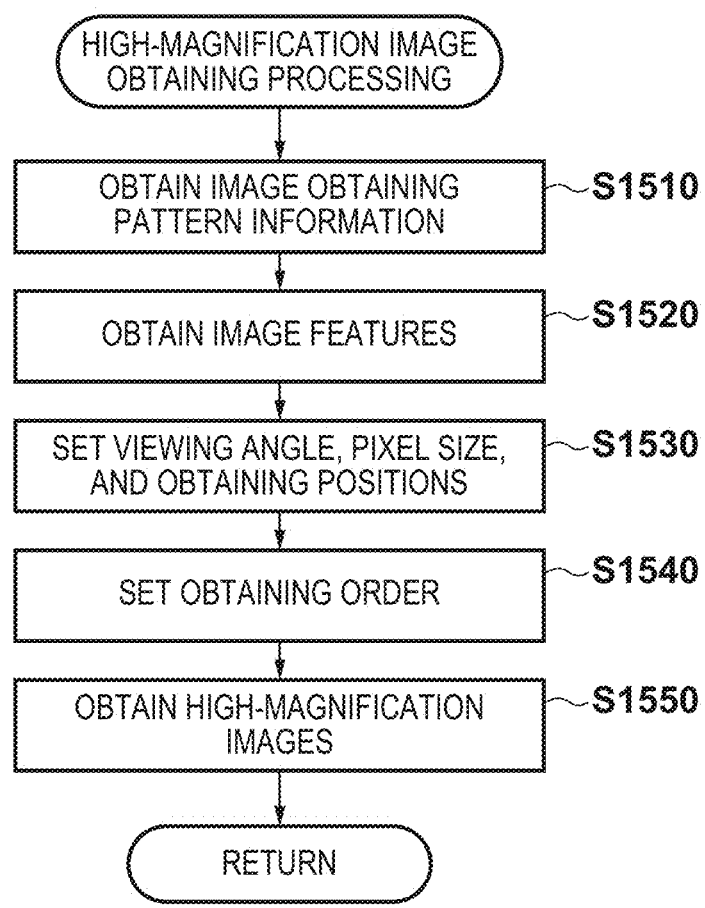
FIG. 16 is a flowchart showing details of image display processing.

Details of the processing (high-magnification image obtaining processing) executed in step S530 will be described next with reference to the flowchart of FIG. 16. Note that step S1510 is the same as in step S810 of the first embodiment, and a description thereof will be omitted.

<Step S1520>

The image feature obtaining unit 134 extracts the boundary positions of an inner limiting membrane B1, a nerve fiber layer boundary B2, an inner plexiform layer boundary B4, a visual cell inner/outer segment boundary B5, and a retinal pigmented layer boundary B6 from the wide viewing angle image $D_L$, that is, the three-dimensional tomogram of the eye stored in the storage unit 120 as image features. FIGS. 7A, 15I, and 15J schematically illustrate the boundary positions B1 to B6. The extracted image features are stored in the storage unit 120.

A feature extraction procedure for the wide viewing angle image $D_L$ will be described here in detail. First, an extraction procedure for extracting layer boundaries will be explained. A three-dimensional tomogram as a processing target is regarded as a set of two-dimensional tomograms (B scan images), and the following processing is performed for each two-dimensional tomogram. Smoothing processing is performed first for a two-dimensional tomogram of interest to remove noise components. Next, edge components are detected from the two-dimensional tomogram, and based on their connectivity, several line segments are extracted as layer boundary candidates. From the extracted candidates, the uppermost line segment is extracted as the inner limiting membrane B1, the second line segment from the upper side is extracted as the nerve fiber layer boundary B2, and the third line segment is extracted as the inner plexiform layer boundary B4. A line segment having the maximum contrast outside (on the side where the z-coordinate is larger in FIG. 7A) the inner limiting membrane B1 is extracted as the visual cell inner/outer segment boundary B5. The lowermost line segment out of the layer boundary candidates is extracted as the retinal pigmented layer boundary B6.

Note that a deformable model by Snakes, a level set method, or the like, may be applied using the line segments as initial values, and more precise extraction may be performed. The layer boundaries may be extracted by a graph cut method. Note that the boundary extraction using a deformable model or graph cuts can be executed three-dimensionally for the three-dimensional tomogram or two-dimensionally for each two-dimensional tomogram. As the method of extracting the layer boundaries, any method is usable as long as it can extract layer boundaries from a tomogram of an eye.

<Step S1530>

A magnification determination unit 1321 determines the magnification type (number of magnifications, viewing angle, and pixel size) of the high-magnification images $D_H$. In this embodiment, the number of magnifications and the pixel size are fixed (1 and 1 [μm]×1 [μm]×1 [μm], respectively), and a detailed description thereof will be omitted. Note that the viewing angle and the pixel size include parameters in the z-axis direction as well, unlike the first embodiment. The viewing angle is a variable parameter. The viewing angle is increased by a threshold Ta [%] only in a high-magnification image in which the distance between the visual cell inner/outer segment boundary B5 and the retinal pigmented layer boundary B6 obtained in step S1520 is equal to or greater than a threshold Trd. The viewing angle is increased to prevent the region important for observation from being uncaptured due to fixation disparity. In addition, since the outer segment portions of visual cells above a retinal detachment region may extend like icicles in the direction of the retinal pigmented layer boundary B6, the viewing angle is increased to allow the whole visual cells to be obtained by high-magnification images.

A position determination unit 1322 determines the obtaining position and the coherence gate position of each high-magnification image $D_{Hj}$. In this embodiment, both are variable parameters. The obtaining position of each high-magnification image $D_{Hj}$ is determined in accordance with the following procedure:

(a) determine the arrangement of the representative position of the image obtaining pattern;

(b) determine the arrangement of the image obtaining pattern in the x-y plane direction; and (c) determine the arrangement of the image obtaining pattern in the z-axis direction.

In (a), the representative position of the image obtaining pattern is set to the center of the image obtaining pattern. The image obtaining pattern is arranged such that the center matches the center-of-gravity position on the retinal detachment region. Note that the retinal detachment region indicates a region obtained by projecting a region where the distance between the visual cell inner/outer segment boundary B5 and the retinal pigmented layer boundary B6 is equal to or larger than the threshold Trd onto the x-y plane.

In (b), the arrangement of each high-magnification image in the x-y direction is determined in accordance with the following procedure such that the retinal detachment region is included in the region of the image obtaining pattern. More specifically, a circle that connects the centers of high-magnification images located on the outermost periphery is obtained. The circle is enlarged up to such a position at which it becomes the circumscribed circle of the retinal detachment region. The x-y direction positions of the high-magnification images are determined such that they fill the circular region at a predetermined interval.

The obtaining positions in the z-axis direction in (c) is determined such that the visual cell inner/outer segment boundary B5 obtained in step S1520 matches the centers of the high-magnification images. The coherence gate of each high-magnification image $D_{Hj}$ is set to, out of settable positions, the position closest to the visual cell inner/outer segment boundary B5 detected in step S1520.

FIG. 15I shows the initial obtaining positions of the image obtaining pattern according to this embodiment. FIG. 15I shows the obtaining positions determined in this step. For the sake of easy recognition of the obtaining pattern, FIGS. 15I and 15J illustrate only the obtaining positions of two columns at the center of the image obtaining pattern. The increase in the viewing angle on the retinal detachment region and overlap of high-magnification images are not illustrated. Note that the types of variable parameters are not limited to those described above, and arbitrary image obtaining parameters can be set as variable parameters.

<Step S1540>

An order determination unit 1324 determines the obtaining order of the high-magnification images $D_{Hj}$. In this embodiment, repetitive processing is performed by setting, out of (i) to (iv) to be described below, (i) as the innermost loop (highest priority), (ii) as the second inner loop, (iii) as the third inner loop, and (iv) as the outermost loop (lowest priority). More specifically, the following procedures (i) to (iv) are executed by setting the obtaining start position (in this embodiment, the upper end of the image obtaining pattern) and the obtaining magnification to the lowest magnification:

(i) obtain images of the same arrangement pattern, same obtaining magnification, and same image obtaining position as many as the repetitive obtaining count;

(ii) move an image of the same arrangement pattern and same obtaining magnification to an adjacent image obtaining position and obtain images again in accordance with the same procedure as (i);

(iii) when (ii) has ended, increase the value of the obtaining magnification, execute the operation (ii) again, and repeat the same operation as many times as the number of magnifications; and (iv) when (iii) has ended, execute the operation (iii) in another arrangement, and repeat the operation until images are obtained in all arrangements.

Note that in the above-described example, no repetitive obtaining is performed in (i) (the obtaining count is only one), and the processing (iv) is omitted because the image obtaining pattern is not a multiple arrangement pattern. The movement to an adjacent image obtaining position in (ii) can be done in an arbitrary direction. In this embodiment, the obtaining position is moved to an adjacent position in the horizontal direction (if no obtaining position exists in the horizontal direction, the position is moved diagonally downward, and if no obtaining position exists diagonally below, either, the position is moved directly downward). That is, the high-magnification images are sequentially obtained from right to left in the first layer from left to right in the second layer, from right to left in the third layer, . . . , out of the high-magnification image obtaining positions. Note that the order determination method of the present invention is not limited to the above-described procedure, and an arbitrary known order setting method is usable.

<Step S1550>

A high-magnification image obtaining unit 112 requests the tomography imaging apparatus 60 to obtain the plurality of high-magnification images $D_{Hj}$ and fixation mark positions $F_{Hj}$ using the image obtaining parameters designated by the determination unit 132. The tomography imaging apparatus 60 obtains the high-magnification images $D_{Hj}$ and the fixation mark positions $F_{Hj}$ and transmits them in response to the obtaining request. The high-magnification image obtaining unit 112 receives the high-magnification images $D_{Hj}$ and the fixation mark positions $F_{Hj}$ from the tomography imaging apparatus 60 via the LAN 30. The high-magnification image obtaining unit 112 stores the received high-magnification images $D_{Hj}$ and fixation mark positions $F_{Hj}$ in the storage unit 120.

Note that, in this embodiment, the obtaining positions of the high-magnification images $D_{Hj}$ are determined using image features associated with visual cell layer boundaries. However, the present invention is not limited to this. For example, the operator may manipulate (move, enlarge, or reduce) the positions in the image obtaining pattern and adjust the obtaining positions at once to determine the obtaining positions, as in the first embodiment.

As described above, when obtaining a plurality of high-magnification adaptive optics OCT tomograms, the ophthalmologic apparatus 10 determines parameter values associated with obtaining of a plurality of high-magnification images based on image features associated with layer shapes extracted from an OCT tomogram having a viewing angle wider than that of the high-magnification images. This makes it possible to efficiently capture tissues, cells, or lesion candidates whose distribution changes depending on the eye to be examined in a range wider than a high-magnification image.

Other Embodiments

In the above-described embodiments, an alignment target image is implemented as an SLO image or a tomogram of an eye. However, the present invention is not limited to this. For example, the wide viewing angle image $D_L$ may be implemented as a fundus camera image, and the high-magnification image $D_H$ may be implemented as an adaptive optics fundus camera image. The images may be implemented as images of different modalities. For example, the wide viewing angle image $D_L$ may be implemented as a wide viewing angle SLO image, and the high-magnification image $D_H$ may be implemented as a projected image of an adaptive optics tomogram. An arrangement in which a multifunction apparatus including the adaptive optics SLO image capture apparatus 20 and the tomography imaging apparatus 60 is directly connected to the ophthalmologic apparatus 10 may be implemented.

Embodiments of the present invention can also be realized by a computer of a system or an apparatus that reads out and executes computer executable instructions recorded on a storage medium (e.g., a non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), a micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), a digital versatile disc (DVD), or a Blu-ray Disc (BD)™), a flash memory device, a memory card, and the like.

While the present invention has been described with reference to embodiments, it is to be understood that the invention is not limited to the disclosed embodiments.

What is claimed is:

1. An information processing apparatus for controlling, in one image capture region, image capture of a plurality of high-magnification images having a viewing angle smaller than the viewing angle of the image capture region, the apparatus comprising:
a presenter configured to present to an operator for selection a plurality of basic patterns each representing a distribution of positions at which to respectively capture high-magnification images;
an adjuster configured to adjust, in accordance with an instruction of the operator, an image capture condition of the plurality of high-magnification images associated with the basic pattern selected from the plurality of basic patterns;
a controller configured to cause an image capture apparatus to capture the plurality of high-magnification images in the image capture region in accordance with the adjusted image capture condition; and
an obtainer configured to analyze an image representing the entire image capture region of a magnification lower than that of the high-magnification images and to obtain information representing a feature of the image,
wherein said adjuster further adjusts the image capture condition based on the information.

2. The apparatus according to claim 1, wherein said adjuster adjusts the image capture condition based on at least one of a position of a point representing the selected basic pattern in the image capture region, a constraint condition designated by the operator and defining a range that the image capture condition can take, and a change amount of the image capture condition designated by the operator.

3. The apparatus according to claim 1, wherein said obtainer obtains the feature of a region included in one of a closed region and an annular region in the image representing the entire image capture region.

4. The apparatus according to claim 1, further comprising a display controller configured to superimpose the plurality of captured high-magnification images on the image representing the entire image capture region and to cause a display to display the images.

5. The apparatus according to claim 4, wherein said display controller causes said display to display at least one blood vessel image out of the captured high-magnification images based on the feature of the image associated with one of a blood vessel and a region where a blood cell moves obtained by said obtainer.

6. The apparatus according to claim 4, wherein said display controller causes said display to display the plurality of captured high-magnification images in synchronism with a periodical timing represented by a biomedical signal measured from a subject.

7. The apparatus according to claim 1, wherein the image capture condition includes at least one of a position to capture the high-magnification image in the image capture region, an order of image capture, the number of images to be captured at the same position, the viewing angle of the high-magnification image, a pixel size of the high-magnification image, the number of frames of image capture, a frame rate, and an in-focus position.

8. The apparatus according to claim 1, further comprising a judger configured to judge a frame in which at least one of a degree of luminance abnormality, a magnitude of distortion, a level of noise with respect to a signal, and a displacement amount with respect to a reference frame exhibits a value not less than a predetermined value as an exceptional frame from frames of the high-magnification image, and a necessity of re-obtaining of the plurality of high-magnification images is determined based on the judgment result.

9. The apparatus according to claim 1, wherein said controller causes the image capture apparatus to capture a tomogram in the image capture region as the high-magnification image.

10. An information processing apparatus for controlling, in one image capture region, image capture of a plurality of high-magnification images having a viewing angle smaller than the viewing angle of the image capture region, the apparatus comprising:
    an obtainer configured to analyze an image representing the entire image capture region of a magnification lower than that of the high-magnification images and to obtain information representing a feature of the image;
    a determining device configured to determine an image capture condition of the plurality of high-magnification images based on the information;
    a controller configured to cause an image capture apparatus to capture the plurality of high-magnification images in the image capture region in accordance with the determined image capture condition; and
    a display controller configured to superimpose the plurality of captured high-magnification images on the image representing the entire image capture region and to cause a display to display the superimposed images in synchronism with a periodical timing represented by a biomedical signal measured from a subject.

11. The apparatus according to claim 10, wherein said obtainer obtains the feature of a region included in one of a closed region and an annular region in the image representing the entire image capture region.

12. The apparatus according to claim 10, wherein said display controller causes said display to display at least one blood vessel image out of the captured high-magnification images based on the feature of the image associated with one of a blood vessel and a region where a blood cell moves obtained by said obtainer.

13. The apparatus according to claim 10, wherein the image capture condition includes at least one of a position to capture the high-magnification image in the image capture region, an order of image capture, the number of images to be captured at the same position, the viewing angle of the high-magnification image, a pixel size of the high-magnification image, the number of frames of image capture, a frame rate, and an in-focus position.

14. The apparatus according to claim 10, further comprising a judger configured to judge a frame in which at least one of a degree of luminance abnormality, a magnitude of distortion, a level of noise with respect to a signal, and a displacement amount with respect to a reference frame exhibits a value not less than a predetermined value as an exceptional frame from frames of the high-magnification image, and a necessity of re-obtaining of the plurality of high-magnification images is determined based on the judgment result.

15. The apparatus according to claim 10, wherein said controller causes the image capture apparatus to capture a tomogram in the image capture region as the high-magnification image.

16. An information processing method executed by an information processing apparatus for controlling, in a given image capture region, image capture of a plurality of high-magnification images having a viewing angle smaller than the viewing angle of the image capture region, the method comprising:
    presenting to an operator for selection a plurality of basic patterns each representing a distribution of positions at which to respectively capture high-magnification images;
    adjusting, in accordance with an instruction of the operator, an image capture condition of the plurality of high-magnification images associated with the basic pattern selected from the plurality of basic patterns;
    causing an image capture apparatus to capture the plurality of high-magnification images in the image capture region in accordance with the adjusted image capture condition; and
    analyzing an image representing the entire image capture region of a magnification lower than that of the high-magnification images to obtain information representing a feature of the image,
    wherein the image capture condition is adjusted based on the information.

17. An information processing method executed by an information processing apparatus for controlling, in a given image capture region, image capture of a plurality of high-magnification images having a viewing angle smaller than the viewing angle of the image capture region, the method comprising:
    analyzing an image representing the entire image capture region of a magnification lower than that of the high-magnification images and obtain information representing a feature of the image;
    determining an image capture condition of the plurality of high-magnification images based on the information;
    causing an image capture apparatus to capture the plurality of high-magnification images in the image capture region in accordance with the determined image capture condition; and
    superimposing the plurality of captured high-magnification images on the image representing the entire image capture region and causing a display unit to display the superimposed images in synchronism with a periodical timing represented by a biomedical signal measured from a subject.

18. A non-transitory computer readable storage medium storing a computer program for causing a computer to control an information processing apparatus for controlling, in one image capture region, image capture of a plurality of high-magnification images having a viewing angle smaller than the viewing angle of the image capture region, the computer program causing the computer to function as units comprising:
    a presenter configured to present to an operator for selection a plurality of basic patterns each representing a distribution of positions at which to respectively capture high-magnification images;
    an adjuster configured to adjust, in accordance with an instruction of the operator, an image capture condition of the plurality of high-magnification images associated with the basic pattern selected from the plurality of basic patterns;

a controller configured to cause an image capture apparatus to capture the plurality of high-magnification images in the image capture region in accordance with the adjusted image capture condition; and an obtainer configured to analyze an image representing the entire image capture region of a magnification lower than that of the high-magnification images and to obtain information representing a feature of the image, wherein said adjuster further adjusts the image capture condition based on the information.

19. A non-transitory computer readable storage medium storing a computer program for causing a computer to control an information processing apparatus for controlling, in one image capture region, image capture of a plurality of high-magnification images having a viewing angle smaller than the viewing angle of the image capture region, the computer program causing the computer to function as units comprising:

an obtainer configured to analyze an image representing the entire image capture region of a magnification lower than that of the high-magnification images and to obtain information representing a feature of the image;

a determining device configured to determine an image capture condition of the plurality of high-magnification images based on the information;

a controller configured to cause an image capture apparatus to capture the plurality of high-magnification images in the image capture region in accordance with the determined image capture condition; and a display controller configured to superimpose the plurality of captured high-magnification images on the image representing the entire image capture region and to cause a display unit to display the superimposed images in synchronism with a periodical timing represented by a biomedical signal measured from a subject.

* * * * *